(12) United States Patent
Yamamoto et al.

(10) Patent No.: US 9,217,731 B2
(45) Date of Patent: Dec. 22, 2015

(54) WELDING INSPECTION METHOD AND APPARATUS THEREOF

(75) Inventors: Setsu Yamamoto, Kanagawa (JP); Takahiro Miura, Kanagawa (JP); Takeshi Hoshi, Kanagawa (JP); Tsuyoshi Ogawa, Kanagawa (JP); Yoshihiro Fujita, Kanagawa (JP); Shozo Hirano, Kanagawa (JP); Kazumi Watanabe, Kanagawa (JP); Satoshi Nagai, Kanagawa (JP); Masahiro Yoshida, Kanagawa (JP); Satoru Asai, Kanagawa (JP); Makoto Ochiai, Kanagawa (JP); Jun Semboshi, Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 328 days.

(21) Appl. No.: 13/111,217

(22) Filed: May 19, 2011

(65) Prior Publication Data

US 2011/0286005 A1 Nov. 24, 2011

(30) Foreign Application Priority Data

May 21, 2010 (JP) .................................. 2010-117584
Dec. 9, 2010 (JP) .................................. 2010-274453

(51) Int. Cl.
*G01B 11/02* (2006.01)
*G01N 29/46* (2006.01)
(Continued)

(52) U.S. Cl.
CPC .............. *G01N 29/46* (2013.01); *B23K 31/125* (2013.01); *G01N 29/2418* (2013.01); *G01N 2291/267* (2013.01)

(58) Field of Classification Search
CPC ..................... G01N 2291/267; G01N 29/2418; B23K 31/125

USPC ............ 356/502, 485–486, 498, 511; 73/655, 73/643
See application file for complete search history.

(56) References Cited

U.S. PATENT DOCUMENTS

| 2,539,526 A | 1/1951 | Sickles |
| 3,241,015 A | 3/1966 | Allen |

(Continued)

FOREIGN PATENT DOCUMENTS

| CN | 101443657 A | 5/2009 |
| GB | 2 185 816 A | 7/1987 |

(Continued)

OTHER PUBLICATIONS

Paper of Takahiro Muira, "National Symposium on Power and Energy Systems" p. 341-342, Jun. 6, 2010.*

(Continued)

*Primary Examiner* — Gregory J Toatley
*Assistant Examiner* — Maurice Smith
(74) *Attorney, Agent, or Firm* — Foley & Lardner LLP

(57) ABSTRACT

A welding inspection method has steps of: generating transmission laser light for generating an ultrasonic wave and transmitting the transmission laser light to an object to be inspected during or after welding operation for irradiation; generating reception laser light for detecting an ultrasonic wave and transmitting the reception laser light to the object to be inspected for irradiation; collecting laser light scattered and reflected at surface of the object to be inspected; performing interference measurement of the laser light and obtaining an ultrasonic signal; and analyzing the ultrasonic signal obtained by the interference measurement. At least one of the transmission laser light generated in the transmission laser light irradiation step and the reception laser light generated in the reception laser light irradiation step is irradiated onto a welded metal part or a groove side surface.

18 Claims, 27 Drawing Sheets

(51) Int. Cl.
*B23K 31/12* (2006.01)
*G01N 29/24* (2006.01)

(56) References Cited

U.S. PATENT DOCUMENTS

| | | | |
|---|---|---|---|
| 3,302,453 A | 2/1967 | Wood et al. | |
| 3,523,171 A | 8/1970 | Belopitov | |
| 3,729,668 A | 4/1973 | Brette | |
| 4,148,275 A | 4/1979 | Benden et al. | |
| 4,217,782 A | 8/1980 | Pont | |
| 4,289,030 A * | 9/1981 | Alers et al. | 73/588 |
| 4,419,562 A | 12/1983 | Jon et al. | |
| 4,428,237 A | 1/1984 | Zeger et al. | |
| 4,473,786 A | 9/1984 | Miyashita et al. | |
| 4,481,824 A | 11/1984 | Fujimoto et al. | |
| 4,558,265 A | 12/1985 | Hayashida et al. | |
| 4,567,769 A * | 2/1986 | Barkhoudarian | 73/643 |
| 4,621,256 A | 11/1986 | Rusk | |
| 4,659,224 A | 4/1987 | Monchalin | |
| 4,908,510 A | 3/1990 | Huggins | |
| 4,924,063 A | 5/1990 | Büchel et al. | |
| 4,928,009 A | 5/1990 | Ikebe et al. | |
| 4,988,945 A | 1/1991 | Nagase | |
| 5,006,694 A | 4/1991 | Handke et al. | |
| 5,138,564 A | 8/1992 | De Jong et al. | |
| 5,161,537 A | 11/1992 | Hashimoto et al. | |
| 5,235,263 A | 8/1993 | Boston et al. | |
| 5,439,157 A * | 8/1995 | Geier et al. | 228/9 |
| 5,460,451 A | 10/1995 | Wadman | |
| 5,537,876 A * | 7/1996 | Davidson et al. | 73/624 |
| 5,546,214 A | 8/1996 | Black et al. | |
| 5,624,588 A | 4/1997 | Terawaki et al. | |
| 5,653,900 A | 8/1997 | Clement et al. | |
| 5,658,476 A | 8/1997 | Gullo et al. | |
| 5,705,554 A | 1/1998 | Chou et al. | |
| 5,747,797 A | 5/1998 | Fujita | |
| 5,777,229 A | 7/1998 | Geier et al. | |
| 5,895,856 A | 4/1999 | Johnson et al. | |
| 5,898,495 A | 4/1999 | Manning | |
| 6,007,687 A | 12/1999 | Ullman et al. | |
| 6,084,202 A | 7/2000 | Okazaki et al. | |
| 6,084,223 A | 7/2000 | Dietz et al. | |
| 6,097,020 A | 8/2000 | Karasaki | |
| 6,125,703 A | 10/2000 | Mac Lauchlan et al. | |
| 6,188,041 B1 | 2/2001 | Kim et al. | |
| 6,545,250 B2 | 4/2003 | Hartmann et al. | |
| 6,555,779 B1 | 4/2003 | Obana et al. | |
| 6,635,843 B1 | 10/2003 | Takeda et al. | |
| 6,639,207 B2 | 10/2003 | Yamamoto et al. | |
| 6,647,792 B2 | 11/2003 | Ogawa | |
| 6,734,392 B2 | 5/2004 | Philipp et al. | |
| 6,817,528 B2 | 11/2004 | Chen | |
| 6,848,312 B2 * | 2/2005 | Georgeson | 73/627 |
| 7,094,989 B2 * | 8/2006 | McJunkin et al. | 219/124.34 |
| 7,297,972 B2 | 11/2007 | Bruland | |
| 7,330,326 B2 | 2/2008 | Hanks | |
| 7,396,706 B2 | 7/2008 | Sun et al. | |
| 7,421,900 B2 | 9/2008 | Karasawa et al. | |
| 7,591,546 B2 | 9/2009 | Morita | |
| 7,619,209 B2 | 11/2009 | Wong et al. | |
| 7,723,639 B2 | 5/2010 | Ellin et al. | |
| 7,728,967 B2 | 6/2010 | Ochiai et al. | |
| 7,875,844 B2 | 1/2011 | Sheu et al. | |
| 7,964,819 B2 | 6/2011 | Bruland | |
| 8,006,560 B2 | 8/2011 | Sano | |
| 8,094,297 B2 | 1/2012 | Ochiai et al. | |
| 8,115,936 B2 | 2/2012 | Ochiai et al. | |
| 8,183,493 B2 | 5/2012 | Batzinger et al. | |
| 8,329,820 B2 | 12/2012 | Hu et al. | |
| 8,357,891 B2 | 1/2013 | Nishida et al. | |
| 2001/0023862 A1 | 9/2001 | Hartmann et al. | |
| 2002/0198622 A1 | 12/2002 | Dinauer et al. | |
| 2003/0218126 A1 | 11/2003 | Shiba | |
| 2004/0069751 A1 | 4/2004 | Yamazaki et al. | |
| 2005/0023434 A1 * | 2/2005 | Yacoubian | 250/200 |
| 2005/0082267 A1 | 4/2005 | Nagai et al. | |
| 2005/0162662 A1 | 7/2005 | Sauerland et al. | |
| 2005/0258149 A1 | 11/2005 | Glukhoy et al. | |
| 2006/0000816 A1 | 1/2006 | Hogan | |
| 2006/0196860 A1 | 9/2006 | Verschueren | |
| 2006/0215175 A1 * | 9/2006 | Yacoubian | 356/502 |
| 2007/0000328 A1 * | 1/2007 | Buttram | 73/597 |
| 2007/0045250 A1 | 3/2007 | Moor et al. | |
| 2007/0068907 A1 | 3/2007 | Batzinger et al. | |
| 2007/0157730 A1 | 7/2007 | Ochiai et al. | |
| 2008/0072674 A1 * | 3/2008 | Ume et al. | 73/627 |
| 2008/0193726 A1 | 8/2008 | Shimada et al. | |
| 2008/0268619 A1 | 10/2008 | Nakamura | |
| 2008/0293220 A1 | 11/2008 | Nakamura | |
| 2009/0007678 A1 * | 1/2009 | Fukutomi et al. | 73/598 |
| 2009/0090187 A1 | 4/2009 | Sano | |
| 2009/0142906 A1 | 6/2009 | Nakamura | |
| 2009/0149002 A1 | 6/2009 | Watanabe et al. | |
| 2009/0166812 A1 | 7/2009 | Ruuttu et al. | |
| 2009/0197395 A1 | 8/2009 | Nakamura et al. | |
| 2009/0215245 A1 | 8/2009 | Nakamura | |
| 2009/0242522 A1 | 10/2009 | Baird et al. | |
| 2009/0277270 A1 * | 11/2009 | Huebler et al. | 73/622 |
| 2009/0289042 A1 | 11/2009 | Ueda | |
| 2009/0298263 A1 | 12/2009 | Watanabe et al. | |
| 2009/0298264 A1 | 12/2009 | Arai et al. | |
| 2009/0309532 A1 | 12/2009 | Ueda | |
| 2010/0051792 A1 | 3/2010 | Sheu et al. | |
| 2010/0155375 A1 | 6/2010 | Dietz et al. | |
| 2010/0199768 A1 | 8/2010 | Ochiai et al. | |
| 2010/0199769 A1 | 8/2010 | Ochiai et al. | |
| 2010/0208248 A1 | 8/2010 | Ochiai et al. | |
| 2010/0301038 A1 | 12/2010 | Weiss et al. | |
| 2011/0210103 A1 | 9/2011 | Bruland et al. | |
| 2011/0240619 A1 | 10/2011 | Hayashi | |
| 2011/0260716 A1 | 10/2011 | Robinson et al. | |
| 2011/0284508 A1 | 11/2011 | Miura et al. | |

FOREIGN PATENT DOCUMENTS

| | | |
|---|---|---|
| JP | 62-043565 A | 2/1987 |
| JP | 04-030474 U | 3/1992 |
| JP | 05-014914 U | 2/1993 |
| JP | 11-101632 A | 4/1999 |
| JP | 2001-071139 A | 3/2001 |
| JP | 2002-071649 A | 3/2002 |
| JP | 2003-098161 A | 4/2003 |
| JP | 2006-200970 A | 8/2006 |
| JP | 2007-017298 A | 1/2007 |
| JP | 2007-057485 A | 3/2007 |
| JP | 2007-090435 A | 4/2007 |
| JP | 2008-122209 A | 5/2008 |
| WO | WO 2009/104811 A1 | 8/2009 |

OTHER PUBLICATIONS

T. Miura, U.S. PTO Office Action, U.S. Appl. No. 13/111,211, dated Feb. 1, 2013, 21 pages.

U.S. Appl. No. 13/111,21, filed May 19, 2011, Miura.

"Proceedings of 2010 Spring Conference, pp. 63 to 64, The Japanese Society for Non-Destructive Inspection".

T. Miura, U.S. PTO Office Action, U.S. Appl. No. 13/11,211, dated Jul. 31, 2013, 27 pages.

T. Miura, U.S. PTO Official Action, U.S. Appl. No. 13/111,211, dated Jan. 9, 2014, 26 pages.

T. Miura, U.S. PTO Official Action, U.S. Appl. No. 13/111,211, dated Oct. 8, 2014, 28 pages.

Partial English Translation of T. Miura et al., "Development of laser-ultrasonic in-process testing technique for thick weld", Japan Society of Mechanical Engineers, No. 10-6, pp. 341-342.

T. Miura, U.S. PTO Official Action, U.S. Appl. No. 13/111,211, dated Apr. 24, 2015, 27 pages.

Makoto Ochiai, "Method of laser ultrasonic and use of testing technique of non-breaking thick weld", Techno 2008, vol. 20, No. 6, pp. 42-50.

(56) References Cited

OTHER PUBLICATIONS

T. Muira et al., "Development of Laser-ultrasonic in-process testing technique for thick weld", Japan Society of Mechanical Engineers, No. 10-6, pp. 341-342.

T. Miura, U.S. PTO Official Action, U.S. Appl. No. 13/111/211, dated May 30, 2014, 27 pages.

Miura et al., U.S. PTO Official Action dated Aug. 6, 2015 which issued in U.S. Appl. No. 13/111,211, 27 pages.

* cited by examiner

WELDING INSPECTION METHOD AND APPARATUS THEREOF

CROSS-REFERENCE TO RELATED APPLICATIONS

This application is based upon and claims the benefit of priority from Japanese Patent Applications No. 2010-117584 filed on May 21, 2010 and No. 2010-274453 filed on Dec. 9, 2010, the entire contents of all of which are incorporated herein by reference.

FIELD

The present invention relates to a welding inspection method using a laser ultrasonic technology and an apparatus therefore.

BACKGROUND

Welding is a technology indispensable for producing a structure and, with recent technological advancement, welding can be made for an object made of a material or having a shape for which it has conventionally been difficult to perform the welding. Meanwhile, it is often the case that inspection itself is difficult to perform since a structure produced with an advanced welding technology tends to have a particular groove shape or complicated surface shape. Under such circumstances, importance of an inspection technology for guaranteeing reliability of a welded structure has been increased more than ever before.

As described above, when an inspection for guaranteeing the quality of a welded part is performed for a technically-difficult welding, such as thick plate welding or welding for a structure having a complicated shape, there may be a case where a portion to be inspected enters an ultrasonically blind area or an access itself of an inspection device to the portion to be inspected is difficult, resulting in failure to perform the inspection. Further, assuming that the inspection is performed during or immediately after the welding for shortening work periods, the following problems arise. That is, in the case where the inspection is performed during the welding, the groove shape that is being subjected to the welding may give influence to ultrasonic wave propagation to a region to be inspected, which significantly restricts available inspection methods if the flaw detection surface is small in area. Even in the case where the inspection is performed immediately after the welding, there may be a case where more than half a day is required for reducing heat influence preventing the inspection from being performed immediately. Thus, the time taken until the start of the inspection is wasted.

As a method for solving the above problems, a technique in which welding quality is inspected during the welding operation is proposed in Jpn. Pat. Appln. Laid-Open Publication No. 2001-71139 (Patent Document 1, the entire content of which is incorporated herein by reference). However, this system uses a probe that contacts the surface of an object to be inspected for transmitting ultrasonic waves to or receiving ultrasonic waves from the object, making it difficult to deal with a structure having a narrow portion or complicated surface. Further, the use of the probe requires a contact medium, such as glycerin or water so as to allow the ultrasonic probe to contact the surface of the object to be inspected, complicating post-processing. Further, in the case where the object to be inspected has a high temperature, a special mechanism for preventing damage of the probe is required.

Jpn. Pat. Appln. Laid-Open Publication No. 2007-17298 (Patent Document 3, the entire content of which is incorporated herein by reference) proposes a system in which an ultrasonic wave generation mechanism is attached to a welding mechanism so as to monitor welding operation. However, in this system, it is necessary to directly set the ultrasonic wave generation mechanism in the welding mechanism, which requires modification of an existing welding apparatus and limits an applicable welding method to spot welding or its similar method. Thus, in this system, it is difficult to perform versatile welding, such as butt/groove welding. This is because this system does not directly detect an indication such as reflection echo from an improperly welded part caused in the actual welding, but detects a change in an ultrasonic signal, so that the improperly welded part cannot be identified. Thus, this system is not suitable for repairing a specific part of the welding.

Further, Proceedings of 2010 Spring Conference, pages 63 to 64, The Japanese Society for Non-Destructive Inspection (Non-Patent Document 1, the entire content of which is incorporated herein by reference) suggests a possibility of the inspection using laser ultrasonic waves immediately after and during the welding. However, the technique disclosed in Non-Patent Document 1 is a two-probe method represented by a TOFD (Time of Flight Diffraction) method, etc., in which two probes are disposed astride a welded part and thus cannot deal with a geometric blind area in ultrasonic wave propagation, such as a portion just below the welded part. Further, the irradiation location of reception laser is limited to the surface of a structure, and aperture synthesis processing is employed for an enhancement in the sensitivity, so that only a structure having a planer laser irradiation area larger than a certain size can be targeted.

Further, Patent Document 3 discloses a technique that uses ultrasonic waves other than a surface wave, such as bottom echo, as a reference signal in measurement using the surface wave. However, for an arrangement in which two probes are disposed astride a welded part or for an object to be inspected having whose bottom surface is not flat and smooth, the bottom echo intensity itself serves as a parameter and thus cannot play a role of the reference signal.

DETAILED DESCRIPTION

Figure 1:
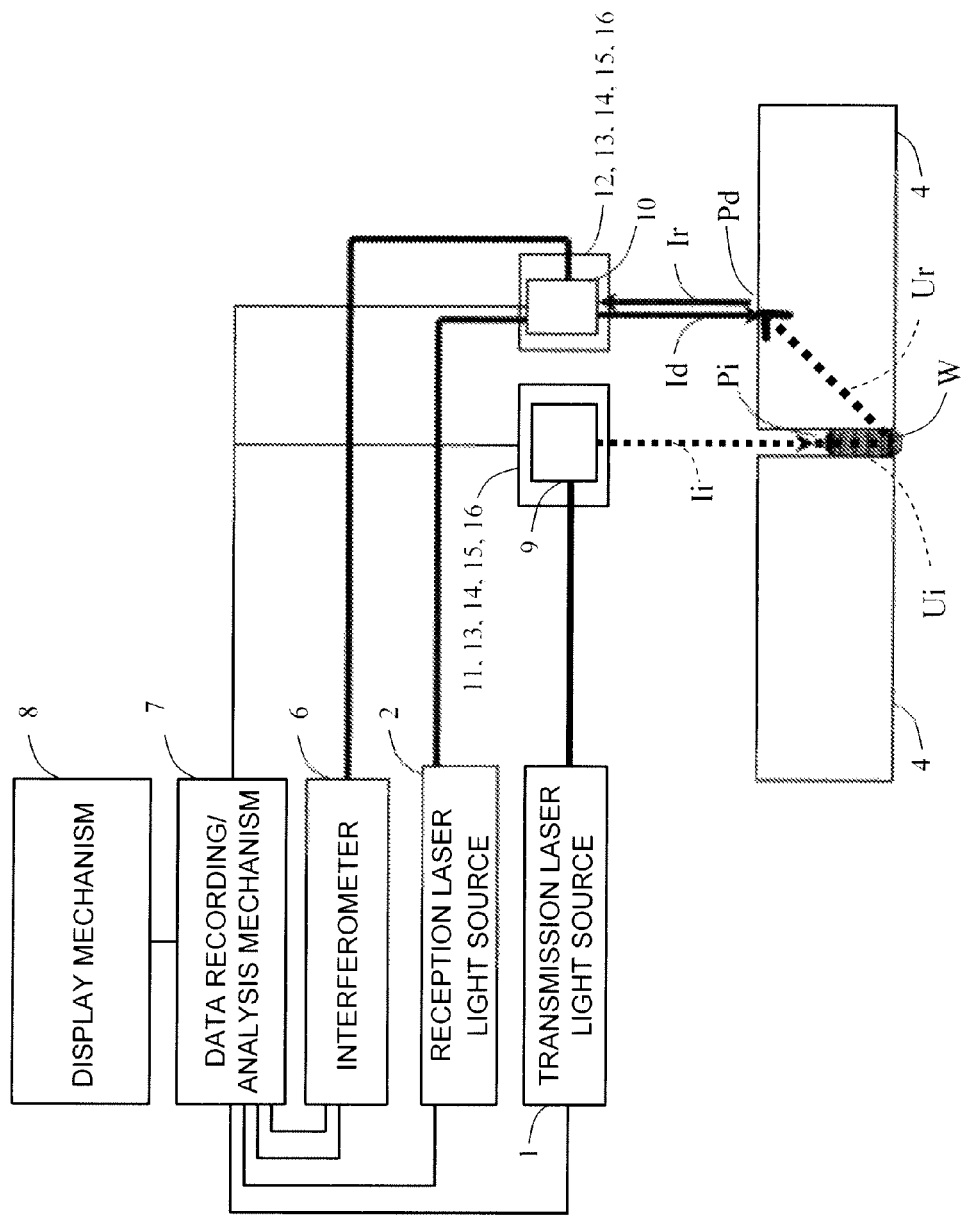
FIG. 1 is a block diagram schematically illustrating a configuration of a welding inspection apparatus according to a first embodiment of the present invention.

The present invention has been made in view of the above problems, and an object thereof is to perform a welding inspection with stable sensitivity even if a portion to be inspected is small in area and even during and immediately after the welding operation at which an object to be inspected has a high temperature.

According to an embodiment, there is provided a welding inspection method comprising: a transmission laser light irradiation step of generating transmission laser light for generating an ultrasonic wave and transmitting the transmission laser light to a predetermined position of an object to be inspected during or after welding operation for irradiation; a reception laser light irradiation step of generating reception laser light for detecting an ultrasonic wave excited by the transmission laser light irradiation step and transmitting the reception laser light to a predetermined position of the object to be inspected for irradiation; a light collection step of collecting laser light scattered and reflected at surface of the object to be inspected; an interference measurement step of performing interference measurement of the laser light collected by the light collection step and obtaining an ultrasonic signal; and an analysis step of analyzing the ultrasonic signal obtained by the interference measurement step. At least one of the transmission laser light generated in the transmission laser light irradiation step and the reception laser light generated in the reception laser light irradiation step is irradiated onto a welded metal part or a groove side surface.

According to another embodiment, there is provided a welding inspection apparatus comprising: a transmission laser light source that generates transmission laser light for generating an ultrasonic wave; a transmission optical mechanism that transmits the transmission laser light to a predetermined position of the object to be inspected during or after welding operation for irradiation; a reception laser light source that generates reception laser light for detecting an ultrasonic wave excited by the transmission laser light; a reception optical mechanism that transmits the reception laser light generated by the reception laser light source to a predetermined position of an object to be inspected during or after welding operation for irradiation and collects laser light scattered and reflected at surface of the object to be inspected; an interferometer that performs interference measurement of the scattered and reflected laser light; a data analysis mechanism that measures and analyzes an ultrasonic signal obtained by the interferometer, at least one of the transmission laser light and the reception laser light being irradiated onto a welded metal part or a groove side surface.

Hereinafter, embodiments of the present invention will be described with reference to the accompanying drawings. Throughout the drawings, the same reference numerals are used for similar or corresponding elements, and redundant explanation will be omitted.

[First Embodiment]

Figure 2:
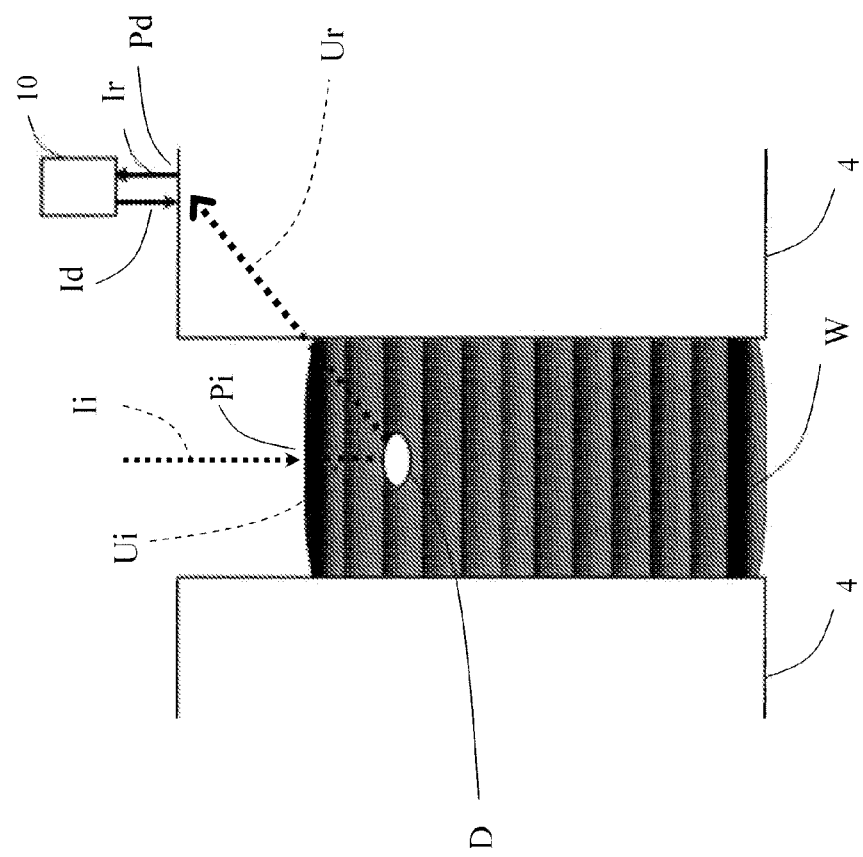
FIG. 2 is a cross-sectional view illustrating the paths of transmission laser light, the reception laser light, the scattered/reflected laser light, and the excited ultrasonic wave in a welding inspection method according to the first embodiment of the present invention.
Figure 3:
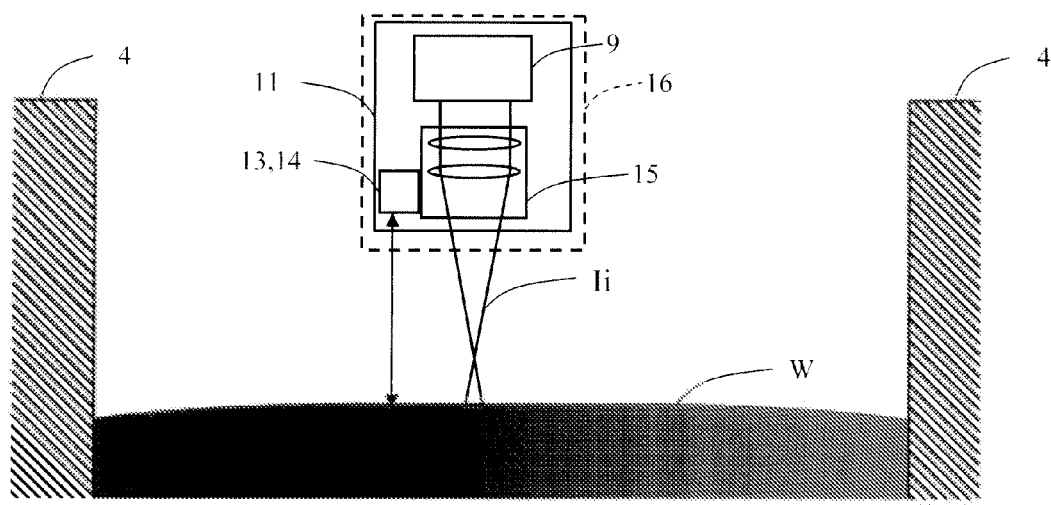
FIG. 3 is a cross-sectional view for explaining functions of a distance measurement mechanism and a focus control mechanism in the welding inspection method according to the first embodiment of the present invention, which illustrates an out-of-focus state.
Figure 4:
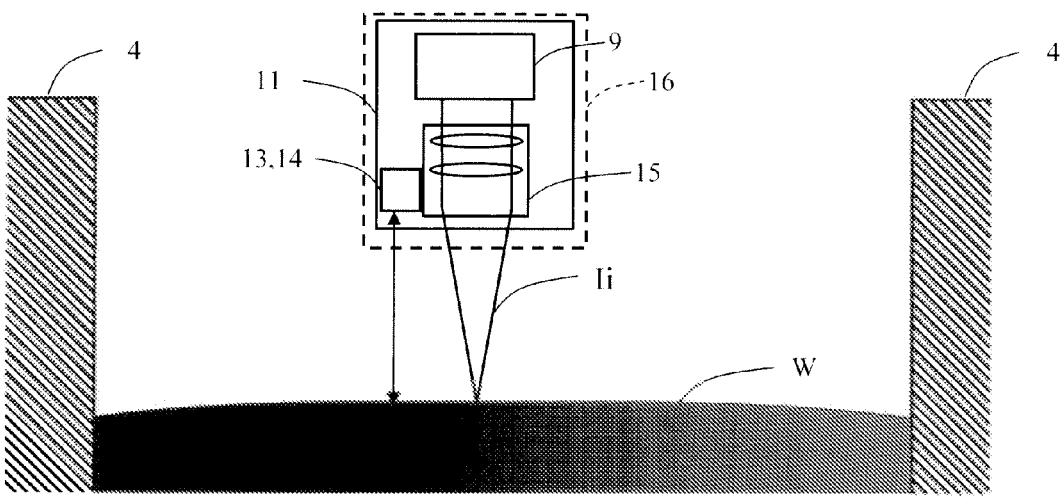
FIG. 4 is a cross-sectional view for explaining functions of the distance measurement mechanism and focus control mechanism in the welding inspection method according to the first embodiment of the present invention, which illustrates an in-focus state.

FIG. 1 is a block diagram schematically illustrating a configuration of a welding inspection apparatus according to a first embodiment. FIG. 2 is a cross-sectional view illustrating the paths of transmission laser light, the reception laser light, the scattered/reflected laser light, and the excited ultrasonic wave in a welding inspection method according to the first embodiment. FIG. 3 is a cross-sectional view for explaining functions of a distance measurement mechanism and a focus control mechanism in the welding inspection method according to the first embodiment, which illustrates an out-of-focus state. FIG. 4 is a cross-sectional view for explaining functions of the distance measurement mechanism and focus control mechanism in the welding inspection method according to the first embodiment, which illustrates an in-focus state.

The welding inspection apparatus according to the present embodiment includes a transmission laser light source 1 for irradiating an object 4 to be inspected with ultrasonic wave transmission laser light (hereinafter, referred to merely as "transmission laser light") Ii, an optical mechanism 9 for transmitting the transmission laser light Ii to a given position on the object 4 to be inspected, and a drive mechanism 11 for moving an irradiation point Pi of the transmission laser light Ii. The welding inspection apparatus further includes a reception laser light source 2 for irradiating the object 4 to be inspected with ultrasonic wave reception laser light (hereinafter, referred to merely as "reception laser light") Id, an optical mechanism 10 for transmitting the reception laser light Id to a given position on the object 4 to be inspected for irradiation and collecting scattered/reflected laser light Ir obtained as a result of scattering/reflection of the reception laser light Id on the surface of the object 4 to be inspected, and a drive mechanism 12 for moving an irradiation point Pd of the reception laser light Id.

The welding inspection apparatus further includes an interferometer 6 for performing interference measurement of the reflected/scattered laser light Ir that has undergone a change from a reflected ultrasonic wave Ur, an apparatus control/data recording/analysis mechanism 7 for recording an ultrasonic signal that has been converted into an electrical signal through the interference measurement so as to perform data analysis, and a display mechanism 8 capable of displaying an obtained inspection result or welding conditions.

The welding inspection apparatus further includes a temperature measurement mechanism 13, a distance measurement mechanism 14, a focus control mechanism 15, and a high-temperature protection mechanism 16 for protecting the optical mechanisms from high temperature.

In the present configuration, the laser used as the transmission laser light source 1 and the reception laser light source 2 may be, for example, Nd:YAG laser, $CO_2$ laser, Er:YAG laser, titanium-sapphire laser, alexandrite laser, ruby laser, dye laser, excimer laser, or other laser sources. The laser light source can output either continuous waves or pulse waves and may be used singularly or in multiples. In the case where a plurality of laser light sources are employed, the number of other components required for measuring ultrasonic waves is increased as needed.

The interferometer 6 may be a Michelson interferometer, a homodyne interferometer, a heterodyne interferometer, a Fizeau interferometer, a Mach-Zehnder interferometer, a Fabry-Perot interferometer, a photorefractive interferometer, or other laser interferometers. As a method other than the interference measurement, a knife-edge method may be adopted. Any of the above interferometers may be used in multiples.

The transmission optical mechanism 9 and the reception optical mechanism 10 are each constituted by lenses, mirrors, and optical fibers. In particular, in the case where the transmission laser light Ii is irradiated onto the surface of the object 4 to be inspected, it is preferable to construct an optical system in which the irradiation diameter at the transmission laser light irradiation point Pi falls within a range of from about 0.1 mm to 30 mm. Alternatively, an optical mechanism may be constituted, in which a cylindrical lens is used so as to make the irradiation shape be linear or elliptic. In this case, it is preferable that the line length falls within a range of from about 1 mm to 100 mm and that the line width falls within a range of about 0.001 mm to 30 mm. The irradiation shape is not limited to one mentioned above.

The optical mechanism 10 is configured such that the irradiation diameter at the reception laser light irradiation point Pd falls within a range of from about 0.1 mm to 10 mm. As illustrated in FIGS. 1 and 2, the transmission laser light Ii and the reception laser light Id are irradiated onto a welded part W of the object 4 to be inspected and outer surface thereof, respectively.

The high-temperature protection mechanism 16 has a function of keeping the temperatures of the optical mechanisms 9 and 10 at a temperature lower than the temperature that gives significant influence on their functions and is constituted by a heat insulator and a cooling mechanism. The heat insulator is selected on the assumption that it is flame-resistant and may be a fiber type heat insulator, a formed heat insulator, a vacuum heat insulator, or other types of heat insulators. The cooling mechanism may be a cooling technology using air-cooling, water-cooling, gas-cooling, coolant such as a gel material or Peltier element, or other cooling technologies. When the surface temperature of the object 4 to be inspected is sufficiently lower than the temperature that gives significant influence on the optical mechanism, the function of the cooling mechanism can be suspended.

The apparatus control/data recording/analysis mechanism 7 has a function of recording ultrasonic wave data obtained by the interferometer 6, a function of analyzing the obtained ultrasonic wave data, a function of displaying and recording position information of the optical mechanisms obtained from the distance measurement mechanism 14, a function of feeding back the position information to the focus control mechanism 15 so as to adjust a laser light irradiation point, a function of recording data obtained from the temperature measurement mechanism 13, a function of determining an inspection result and transmitting a feedback signal to a welding control mechanism 5 of a welding mechanism 3, and the like. The apparatus control/data recording/analysis mechanism 7 may be one or more mechanisms and the abovementioned functions may be implemented in a plurality of apparatus control/data recording/analysis mechanism 7 in a distributed manner.

The drive mechanisms 11 and 12 can move or rotate the optical mechanisms 9 and 10 about one or more axes to thereby make them to access a narrow portion such as a welding groove and a complicated shape portion.

The display mechanism 8 has one or more functions out of displaying an inspection result, displaying an alarm when it has been determined that there is a response indicating occurrence of a defect D, urgently stopping the operation through a touch panel interface, and the like.

The temperature measurement mechanism 13 may be, e.g., a non-contact radiation thermometer, a contact type thermometer such as a resistance thermometer, a thermistor, a thermocouple, or a technique for measuring the temperature according to other principles. Further, the number of the temperature measurement mechanisms 13 provided may be one or more. In the case where a non-contact type is used, the temperature measurement mechanism 13 is preferably installed on the propagation paths of an incident ultrasonic wave Ui and a reflected ultrasonic wave Ur or portions near the propagation paths. In the case where a contact type is used, the temperature measurement mechanism 13 is preferably installed at portions near the propagation paths of the incident ultrasonic wave Ui and reflected ultrasonic wave Ur such that the temperature measurement mechanism 13 itself does not act as a disturbance element.

The transmission laser light Ii emitted from the transmission laser light source 1 passes through the optical mechanism 9 and is irradiated onto the surface of the object 4 to be inspected. At this time, the incident ultrasonic wave Ui is generated due to reactive force against heat strain or abrasion of a superficial layer. The incident ultrasonic wave Ui generated includes various modes such as a longitudinal wave, a transverse wave, and a surface wave and is hereinafter collectively referred to as incident ultrasonic wave Ui. When the generated incident ultrasonic wave Ui reaches the defect D or bottom surface of the object to be inspected, the propagation path changes due to reflection, scattering, and refraction of the ultrasonic wave, and the incident ultrasonic wave Ui becomes the reflected ultrasonic wave Ur which is a response from the defect D. The response generated includes various modes such as a longitudinal wave, a transverse wave, and a surface wave and is hereinafter collectively referred to as reflected ultrasonic wave Ur.

Meanwhile, the reception laser light Id emitted from the reception laser light source 2 passes through the optical mechanism 10 and is irradiated onto the surface of the object 4 to be inspected. At this time, when the reflected ultrasonic wave Ur reaches the reception laser light irradiation point Pd, the reception laser light Id undergoes amplitude modulation or phase modulation, or a change in the reflection angle and reflected as the scattered/reflected laser light Ir containing an ultrasonic signal component.

The scattered/reflected laser light Ir having the ultrasonic signal is collected once again by the optical mechanism 10 and then transmitted to the interferometer 6. The optical signal having the ultrasonic component is converted into an electrical signal by interferometer 6 and then stored as ultrasonic wave data by the apparatus control/data recording/analysis mechanism 7. The apparatus control/data recording/analysis mechanism 7 can apply averaging processing, moving average processing, filtering, FFT (Fast Fourier Transform), wavelet transformation, aperture synthesis processing, and other signal processing to the obtained ultrasonic signal. Further, the ultrasonic signal can be corrected using welding position information, irradiation position information, temperature information, and the like.

Figure 5:
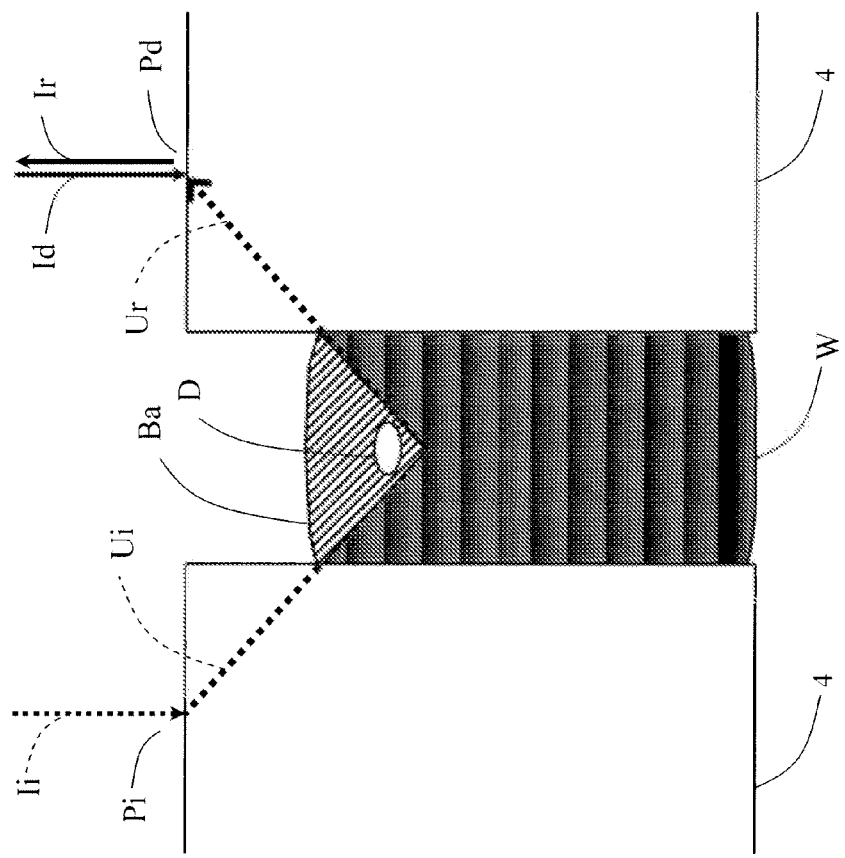
FIG. 5 is a cross-sectional view illustrating the paths of transmission laser light, the reception laser light, the scattered/reflected laser light, and the excited ultrasonic wave in a welding inspection method of a comparison example.

A reason why the region for which the flaw detection has been impossible in a conventional approach can now be inspected by the above system will be described. FIG. 5 is a cross-sectional view illustrating the paths of transmission laser light, the reception laser light, the scattered/reflected laser light, and the excited ultrasonic wave in a welding inspection method of a comparison example. FIG. 5 illustrates a two-probe method represented by a TOFD-UT, in which two probes were disposed astride the welded part W. In the case where a product being welded or a finished product has a shape as illustrated, a portion just below the groove enters an ultrasonically blind area Ba, so that the defect D is difficult to detect if it exists at this portion. In this case, if the welding operation has not yet been completed, the welding operation advances with the defect D existing inside the product. Thus, when the defect is detected, a great deal of time is required for a reversion process. If the welding operation has already been completed, the defect D remains at a portion near the outer surface, which may result in a failure to satisfy required strength.

In the present embodiment, as illustrated in FIGS. 1 and 2, the transmission laser light irradiation point Pi is located on the surface of a welded metal part (welding beads) W of the object 4 to be inspected. As illustrated in FIG. 2, the incident ultrasonic wave Ui directly enters the defect D just below the incident point, and the reflected ultrasonic wave (scattered wave) Ur from the defect D propagates in the object 4 to be inspected as bulk waves such as longitudinal waves or transverse waves. Components of the bulk waves can be received by the reception laser light Id irradiated on the outer surface of the object 4 to be inspected. This allows flaw detection for a portion which has been blind in a conventional approach.

In this case, the transmission ultrasonic wave excitation position is nearer to the defect D than in the case of a conventional arrangement, so that it is possible to minimize a reduction in the sensitivity due to attenuation corresponding to the propagation distance.

The sound velocity of an obtained ultrasonic signal can be corrected by the temperature measurement mechanism 13. In general, the sound velocity of the ultrasonic wave depends on the temperature. Therefore, there occurs an error when the welding defect position is calculated from the detected ultrasonic signal. Similarly, there occurs a large error when signal processing using ultrasonic signal transmission/reception position information, such as the aperture synthesis processing, is performed. In order to prevent this, the temperature of the object to be inspected at the inspection time is measured, and a previously prepared calibration formula, etc., for adjusting a change in the sound velocity due to a temperature change is used to correct the sound velocity. With this configuration, it is possible to reduce an error due to the temperature change.

When a distance between the object 4 to be inspected and the optical mechanism 9 or distance between the object 4 to be inspected and the optical mechanism 10 is changed during the welding, the collection efficiency of the scattered/reflected laser light Ir containing the ultrasonic signal may be degraded. Further, the above change in the distance may cause a change in the irradiation spot diameter of the transmission laser light Ii or the reception laser light Id as illustrated in FIG. 3 or a change in the position of the transmission laser light irradiation point Pi or the reception laser light irradiation point Pd. This incurs a reduction in the excitation efficiency of the ultrasonic wave to be generated, a reduction in the reception sensitivity, error in the correction processing using the position information which is performed at the time of the signal processing such as the aperture synthesis processing, which constitutes a factor adversely affecting the sensitivity. In order to prevent this, the distance change amount is measured by using the distance measurement mechanism 14 as illustrated in FIG. 4, and the measurement results are fed back to the drive mechanisms 11 and 12 and the focus control mechanism 15, so as to adjust the distance therebetween to an optimum value, whereby a reduction in the sensitivity can be prevented.

If the groove is narrow, the optical mechanisms 9 and 10 need to be brought close to the object 4 to be inspected. At this time, the high-temperature protection mechanism 16 is used to keep the temperatures of the optical mechanisms 9 and 10 at a temperature lower than the temperature that gives significant influence on their functions, allowing the measurement to be performed even during and immediately after the welding operation at which an object 4 to be inspected has a high temperature.

As described above, according to the first embodiment, it is possible to perform the welding inspection with stable sensitivity even if a portion to be inspected is small in area and even if the object to be inspected has a high temperature.

[Second Embodiment]

Figure 6:
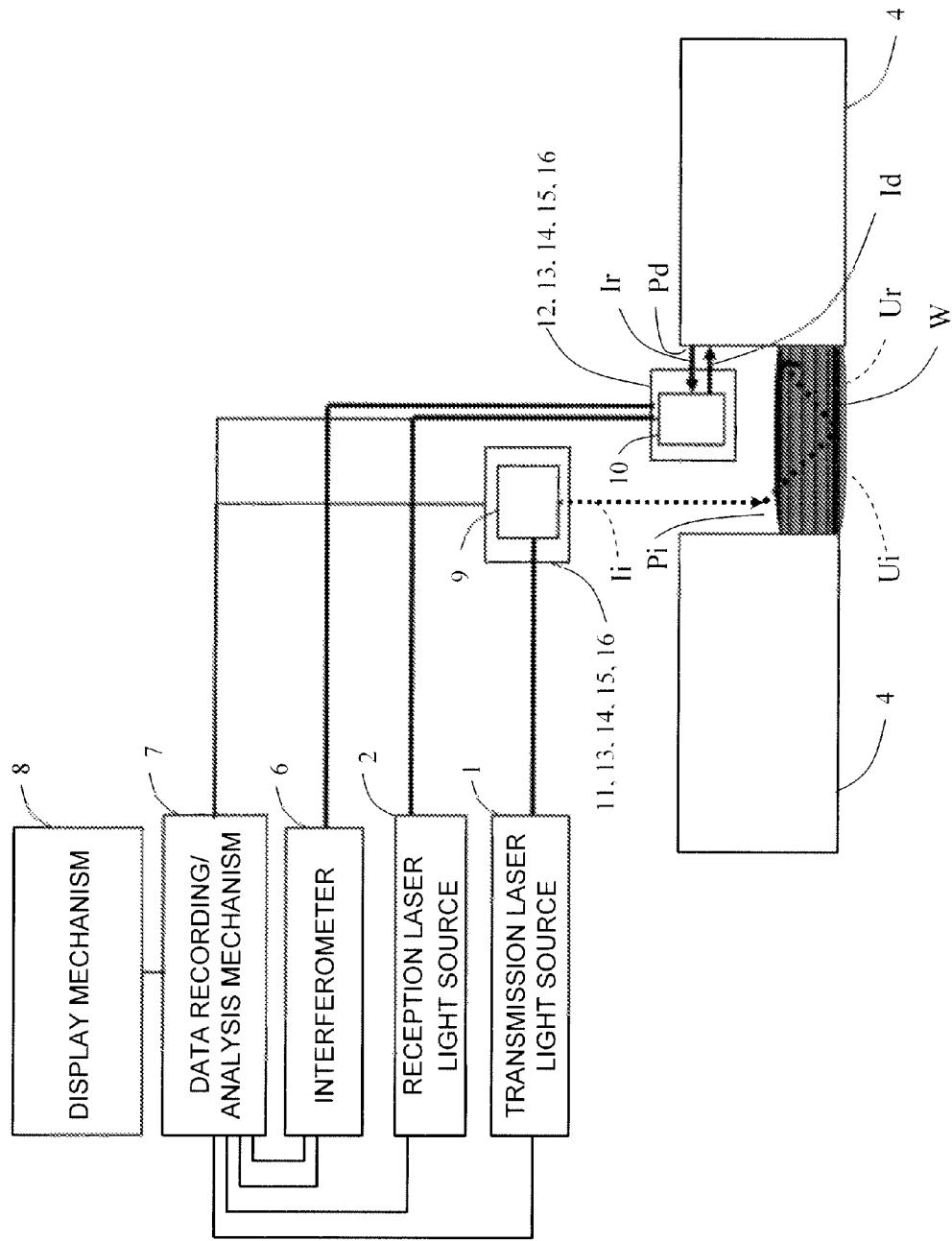
FIG. 6 is a block diagram schematically illustrating a configuration of the welding inspection apparatus according to a second embodiment of the present invention.
Figure 7:
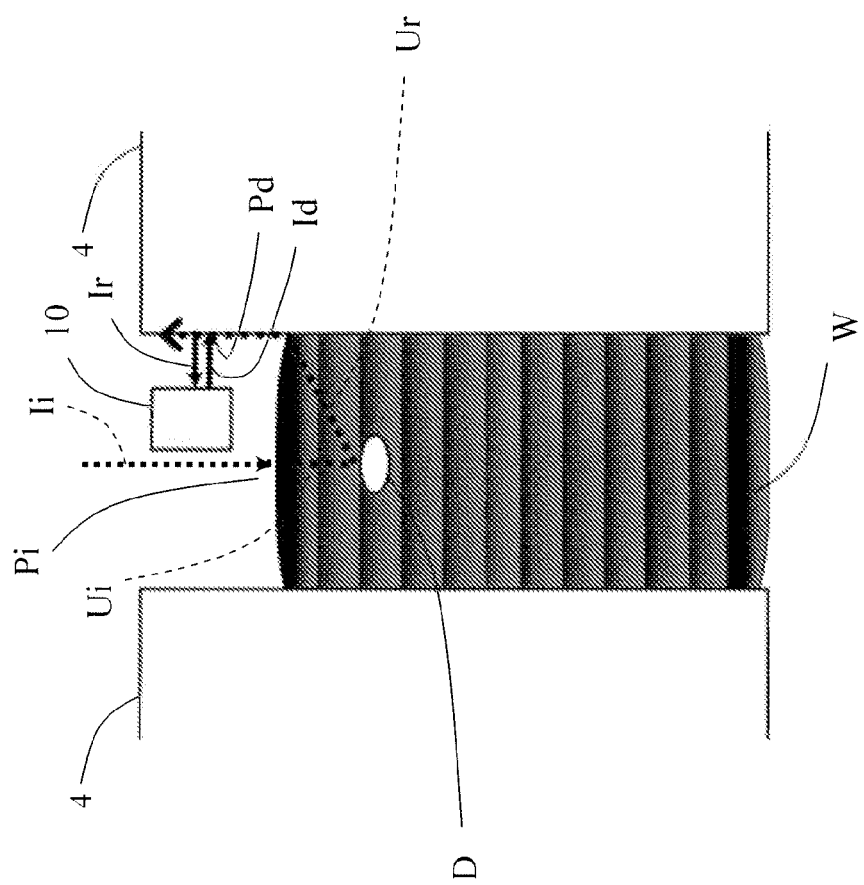
FIG. 7 is a cross-sectional view illustrating the paths of the transmission laser light, the reception laser light, the scattered/reflected laser light, and the excited ultrasonic wave in the welding inspection method according to the second embodiment of the present invention.

FIG. 6 is a block diagram schematically illustrating a configuration of the welding inspection apparatus according to a second embodiment of the present invention. FIG. 7 is a cross-sectional view illustrating the paths of the transmission laser light, the reception laser light, the scattered/reflected laser light, and the excited ultrasonic wave in the welding inspection method according to the second embodiment.

In the present embodiment, the reception laser light Id is irradiated onto the groove side surface. In this case, the incident ultrasonic wave Ui directly enters the defect D just below the incident point, and reflected ultrasonic wave Ur from the defect D propagates in the object 4 to be inspected as bulk waves such as longitudinal waves or transverse waves. Surface wave components whose mode has been converted at the groove portion can be received by the reception laser light Id irradiated onto the groove side surface. This allows flaw detection for a portion which has been blind in a conventional approach.

In the present embodiment, although the optical mechanism 10 needs to be brought close to the object 4 to be inspected, the high-temperature protection mechanism 16 is used to keep the temperature of the optical mechanism 10 at a temperature lower than the temperature that gives significant influence on its function, allowing the measurement to be performed even during and immediately after the welding operation at which an object 4 to be inspected has a high temperature. Further, the apparatus size can be reduced as compared with the first embodiment.

The configurations and functions other than described above in the present embodiment are the same as those in the first embodiment.

[Third Embodiment]

Figure 8:
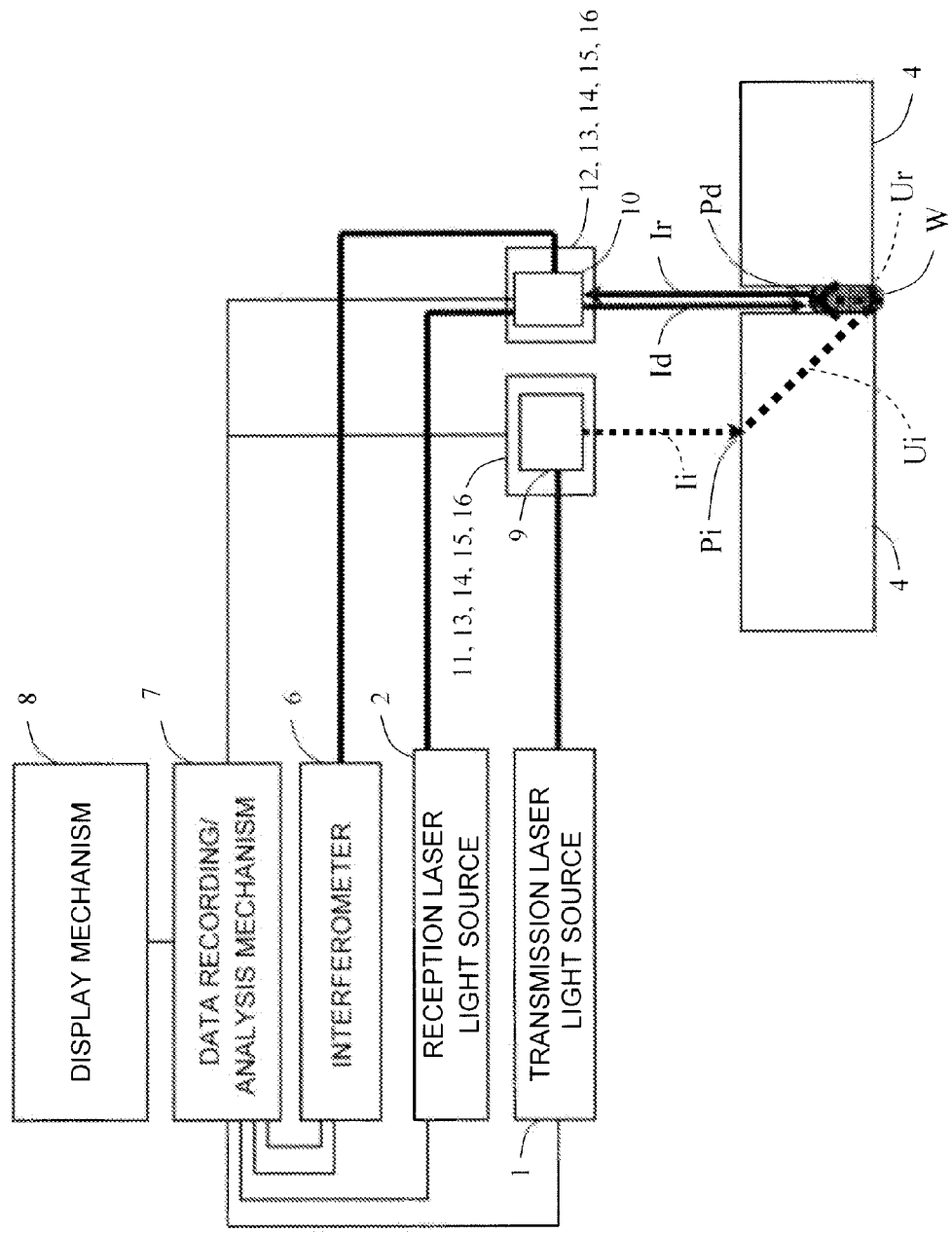
FIG. 8 is a block diagram schematically illustrating a configuration of the welding inspection apparatus according to a third embodiment of the present invention.

FIG. 8 is a block diagram schematically illustrating a configuration of the welding inspection apparatus according to a third embodiment of the present invention. In the present embodiment, the positional relationship between the transmission laser light irradiation point Pi and the reception laser light irradiation point Pd in the first embodiment is reversed so as to locate the reception laser light irradiation point Pd on the surface of the welded metal part W of the object 4 to be inspected. The configurations other than this are the same as those in the first embodiment. The same effects can be obtained even when the positions of the transmission laser light irradiation point Pi and the reception laser light irradiation point Pd are reversed.

[Fourth Embodiment]

Figure 9:
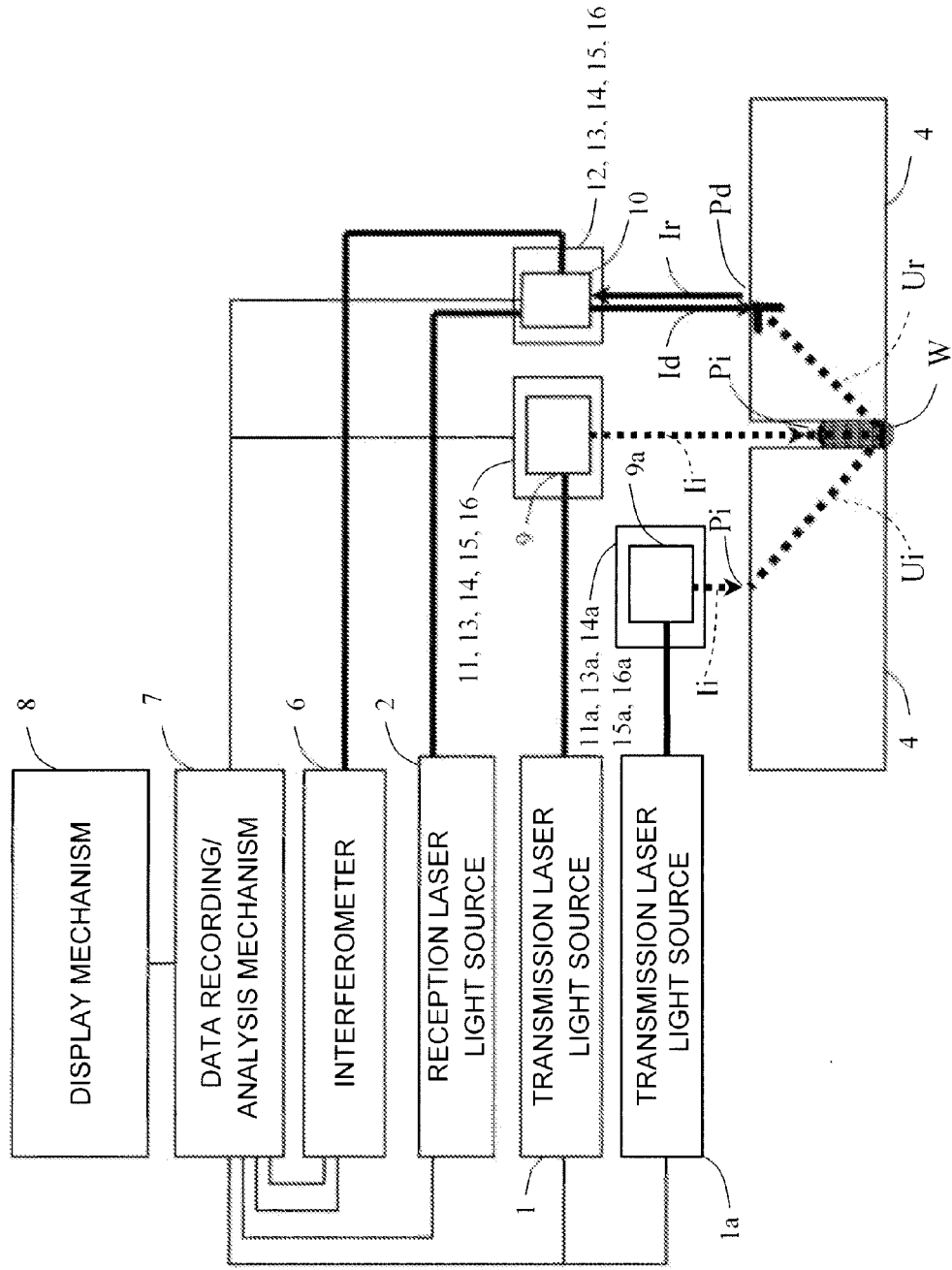
FIG. 9 is a block diagram schematically illustrating a configuration of the welding inspection apparatus according to a fourth embodiment of the present invention.

FIG. 9 is a block diagram schematically illustrating a configuration of the welding inspection apparatus according to a fourth embodiment of the present invention. In the present embodiment, another set of the transmission laser light source 1 in the first embodiment and its associated components or components same as the optical mechanism 9, drive mechanism 11, temperature measurement mechanism 13, distance measurement mechanism 14, focus control mechanism 15, and high-temperature protection mechanism 16 is provided. The transmission laser light irradiation point Pi set by an added transmission laser light source 1a and a drive mechanism 11a is located on the surface of the object 4 to be inspected and not on the surface of the welded metal part W.

According to the present embodiment, the same inspection as in the first embodiment can be performed. Further, the inspection based on the conventional positional relationship (FIG. 5) between the transmission laser light irradiation point Pi and the reception laser light irradiation point Pd can be performed. As a result, the entire range from a portion just below the groove to the bottom surface of the object 4 to be inspected can be inspected.

Further, by using two or more transmission laser light sources so as to perform the transmission laser light irradiation from a plurality of different transmission laser light irradiation points Pi, it is possible to perform the inspection over a wide range. Further, a system in which both the arrangement and the number of components are interchanged between the transmission and the reception sides can be constructed.

[Fifth Embodiment]

Figure 10:
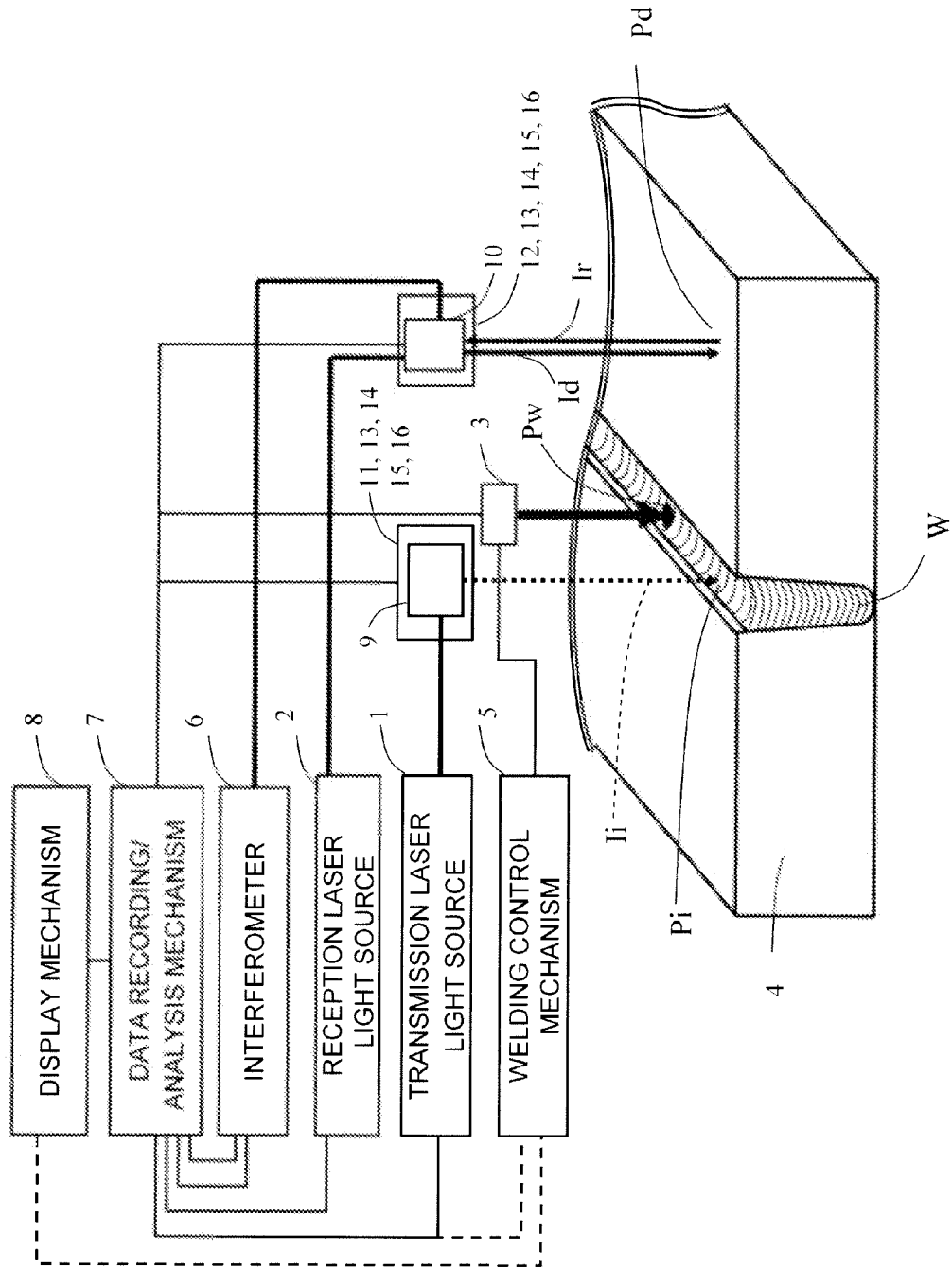
FIG. 10 is a block diagram schematically illustrating a configuration of a welding system including the welding inspection apparatus according to the fifth embodiment of the present invention.
Figure 11:
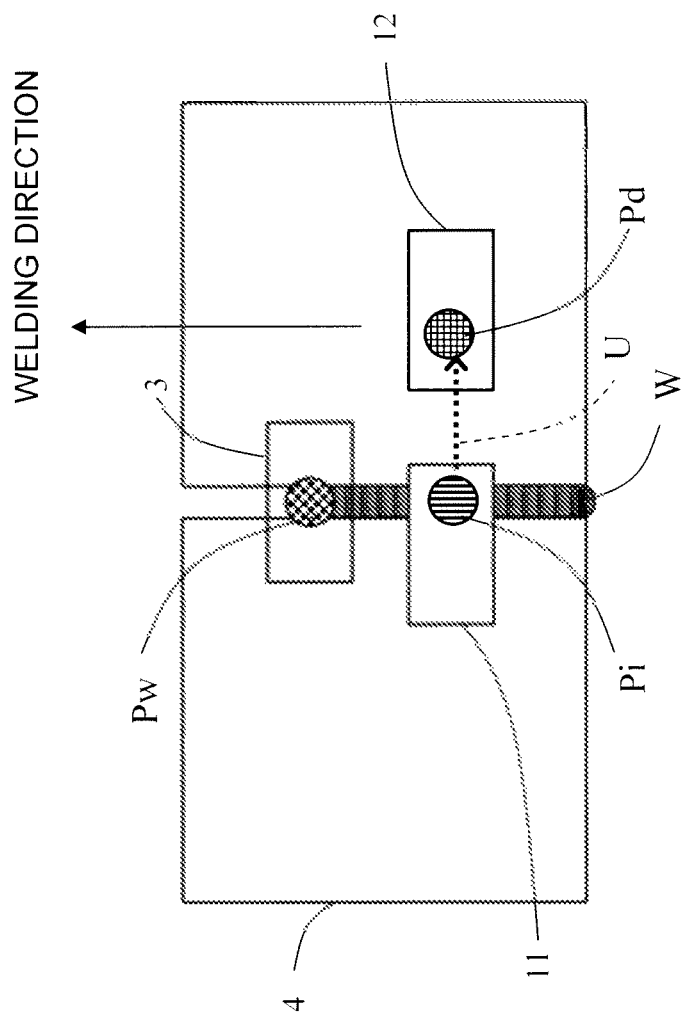
FIG. 11 is a plan view illustrating a positional relationship among the welded part, the transmission laser light irradiation point, the reception laser light irradiation point in the welding system according to the fifth embodiment of the present invention.
Figure 12:
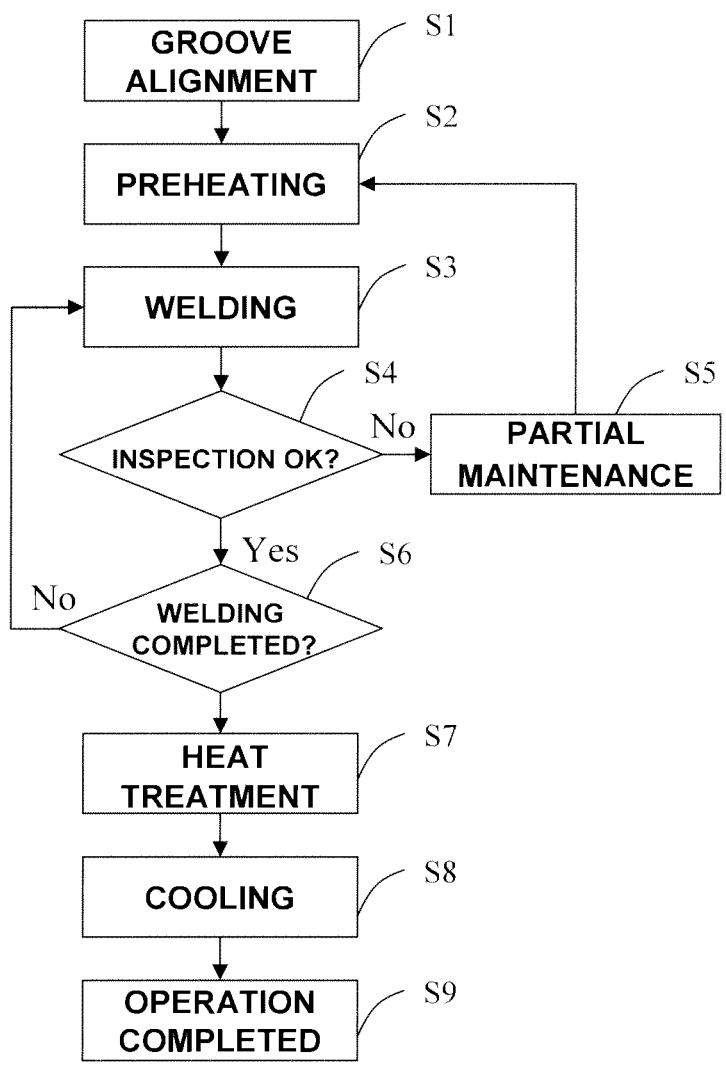
FIG. 12 is a flowchart illustrating a procedure of the welding inspection method according to the fifth embodiment of the present invention.

A fifth embodiment of the present invention will be described. FIG. 10 is a block diagram schematically illustrating a configuration of a welding system including the welding inspection apparatus according to the fifth embodiment of the present invention. FIG. 11 is a plan view illustrating a positional relationship among the welded part, the transmission laser light irradiation point Pi, the reception laser light irradiation point Pd in the welding system according to the fifth embodiment. FIG. 12 is a flowchart illustrating a procedure of the welding inspection method according to the fifth embodiment.

In the present embodiment, a welding mechanism 3 and a welding control mechanism 5 are added to the welding inspection apparatus according to the first embodiment.

The welding mechanism 3 covers: general arc welding methods such as shielded metal arc welding, submerged arc welding, inert gas arc welding, TIG welding, MAG welding, MIG welding, $CO_2$ arc welding, plasma-arc welding, and electroslag welding; general resistance welding methods such as spot welding and seam welding; special welding methods such as gas welding, thermit welding, electron beam welding, and laser welding; and general metal bonding technologies represented by friction-stir bonding such as crimping or brazing.

With the above configuration, the welding operation and welding inspection can be performed simultaneously. A procedure of the welding operation will be described below along the flowchart of FIG. 12. Groove alignment is performed (step S1), the object to be welded is preheated (step S2), and then welding is performed (step S3). In parallel, the welding inspection is performed (step S4). When a problem arises as a result of the welding inspection, partial maintenance and repair, such as elimination or melting of the welded part W is made (step S5), followed by the preheating (step S2) and welding processes (step S3) once again. When a result of the inspection welding (step S4) has indicated that the welding is completed without any problem, the welding is ended (step S6). After the end of the welding, the object to be welded is heated (step S7) and then cooled (step S8), whereby the entire operation is completed (step S9).

A determination of presence/absence of the welding defect in the welding inspection (step S4) may be made automatically by the apparatus control/data recording/analysis mechanism 7 based on the analysis result (for example, based on a threshold value on the ultrasonic signal, based on a comparison between a simulation result and real data, etc.) or made by an operator based on the display on the display mechanism 8.

In the partial maintenance and repair process (step S5), the welding position may be set back to a location before the improperly welded part once during the welding operation for rewelding, or only the improperly welded part may be subjected to the rewelding after a series of the welding processing is ended. Further, rewelding may be performed after partial cutting/removal by gauging or the like.

Further, during or after the partial maintenance and repair process (step S5), welding conditions may be altered so as not to cause the welding defect to occur.

As described above, in this process flow, the inspection is performed during the welding and, in the case where the welding defect is detected from the inspection result, only the improperly welded part is subjected to maintenance and repair followed by another welding.

In a conventional process flow, the inspection can be performed only after the completion of the welding and application of heat treatment/cooling treatment and, thus, in the case where the number of welding passes is large, the time required until the inspection starts becomes enormous. In addition, execution of the reprocessing becomes a major burden. On the other hand, according to the present embodiment, the inspection can be performed for each welding pass or after completion of a specified number of welding passes, so that if the welding defect occurs, the burden of the reprocessing for rewelding is small. Further, a configuration may be possible in which it can be determined that there is no problem in terms of structural strength although the welding defect occurs. Further, the inspection can be performed not only for a hardened state after the welding but also for a state of melting.

The above process flow may be modified as follows: a minor welding defect is detected as a result of the welding inspection (step S4); the partial maintenance and repair (step S5) for the welded part W is not performed since the detected welding defect is tolerable; and welding conditions are changed (not illustrated) while the welding (step S3) is being continued.

A determination whether the welding defect is tolerable or not is made as follows. That is, when a signal representing the welding defect based on a threshold determination is observed a predetermined number of times or more, or a predetermined time length or more in a predetermined region as a result of the analysis performed by the apparatus control/data recording/analysis mechanism 7, it is determined that a welding defect exceeding a tolerable range has occurred, while when the signal representing the welding defect is observed less than a predetermined number of times, or less than a predetermined time length, it is determined that a welding defect within a tolerable range has occurred.

Also in the welding inspection (step S4) of FIG. 12, when the welding defect is within a tolerable range, the process flow may advance to step S6, while when the welding defect exceeds a tolerable range, the process flow may advance to step S5.

As described above, the inspection result can be fed back to the welding control mechanism 3 so that the current welding conditions become optimum. Further, the inspection can be performed not only for a hardened state after the welding but also for a state of melting, it is possible to change the current welding conditions to optimum welding conditions and to set such welding conditions as to eliminate the welding defect in the next welding pass. This makes it possible to reduce the welding operation time and cost even if the welding defect occurs.

As described above, it is possible to perform the inspection in real time during the welding without influencing a conventional welding apparatus and, further, to temporarily stop the welding depending on the inspection result and to feed back the inspection result to the current welding conditions.

The process flows of FIG. 12 may be altered such that it is determined in the partial maintenance and repair (step S5) whether the preheating needs to be performed or not after the partial maintenance and repair and, when it is determined that the preheating is not necessary, the welding process (step S3) is performed skipping the preheating (step S2).

According to the present embodiment, the inspection is performed during the welding and, in the case where the welding defect D is detected from the inspection result, only the part corresponding to the defect D is subjected to cutting followed by another welding. In a conventional process flow, the inspection can be performed only after the completion of the welding and application of heat treatment/cooling treatment and, thus, in the case where the number of welding passes is large, the time required until the inspection starts becomes enormous. In addition, execution of the reprocessing becomes a major burden.

On the other hand, according to the present embodiment, the inspection can be performed for each welding pass or after completion of a specified number of welding passes, so that if the defect D occurs, the burden of the reprocessing for rewelding is small. Further, the point Pi onto which the transmission laser light Ii is irradiated may change in shape due to evaporation (abrasion) of the surface of the welded part; however, in the case where multilayer welding is performed, a welding point Pw passes through the point Pi and thereby the influence of the evaporation (abrasion) can be removed. At this time, the influence of a change in the surface by the transmission laser light Ii is sufficiently small and give little influence on the welding itself.

[Sixth Embodiment]

Figure 13:
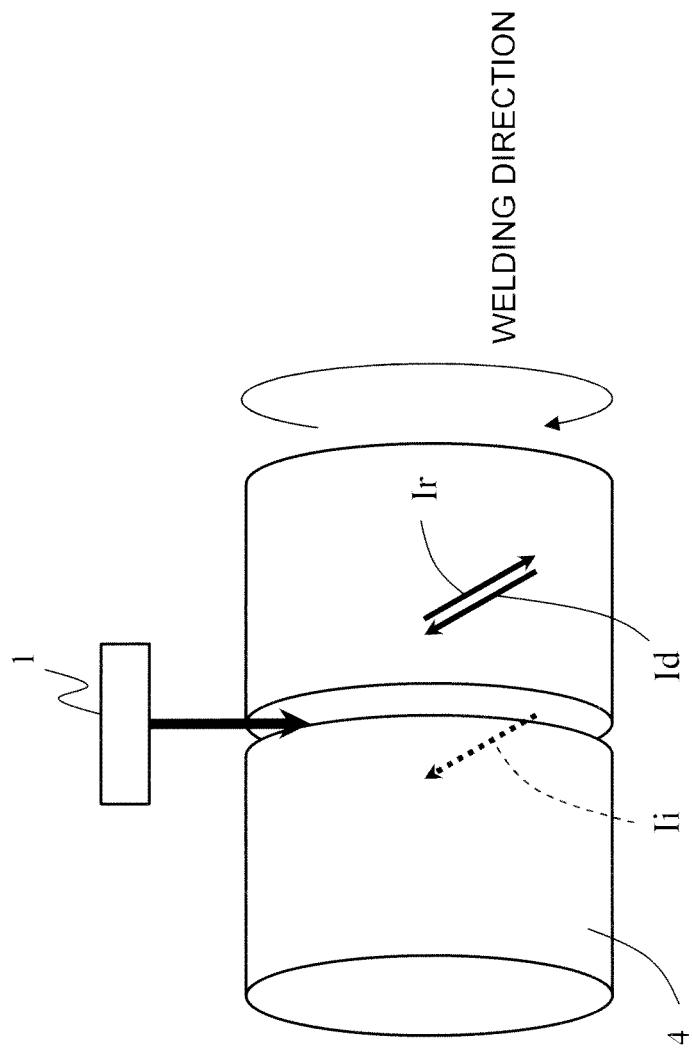
FIG. 13 is a perspective view illustrating a state where the welding inspection method according to a sixth embodiment of the present invention is executed.

FIG. 13 is a perspective view illustrating a state where the welding inspection method according to a sixth embodiment of the present invention is executed. The sixth embodiment is a modification of the fifth embodiment. In the fifth embodiment, the object to be welded, i.e., object to be inspected is constituted by two flat plates. On the other hand, in the sixth embodiment, the object to be welded, i.e., object to be inspected is constituted by two cylinders abutted with each other in the axial direction thereof. Also in this case, it is possible to perform the welding operation while performing the inspection of the welded part W in the same manner as in the fifth embodiment.

[Seventh Embodiment]

Figure 14:
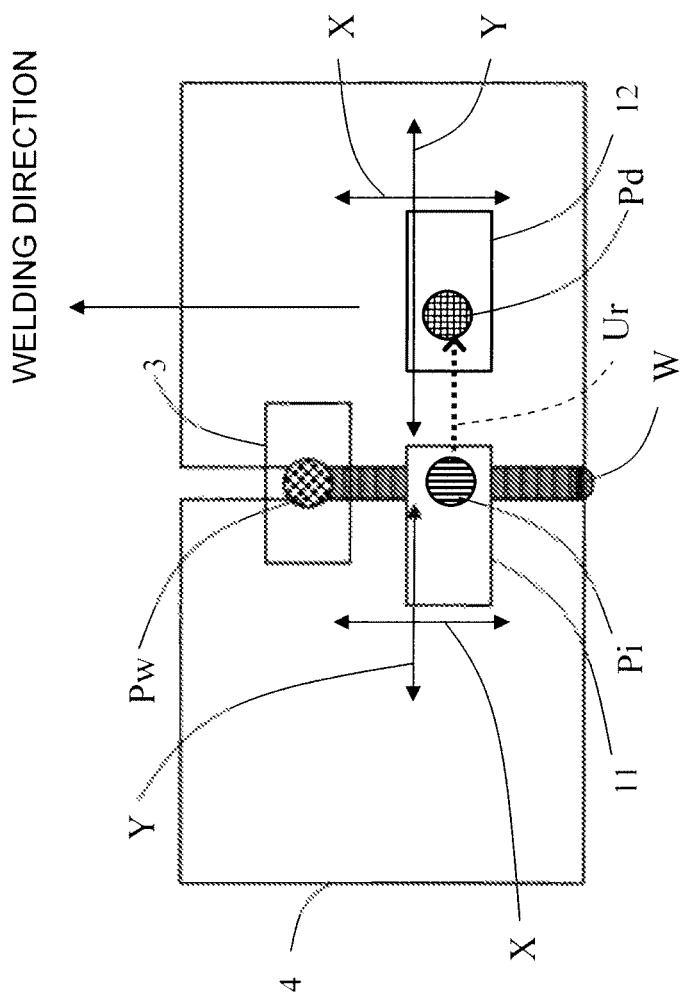
FIG. 14 is a plan view illustrating a positional relationship among the welded part, the transmission laser light irradiation point, the reception laser light irradiation point in the welding inspection apparatus according to a seventh embodiment of the present invention.
Figure 15:
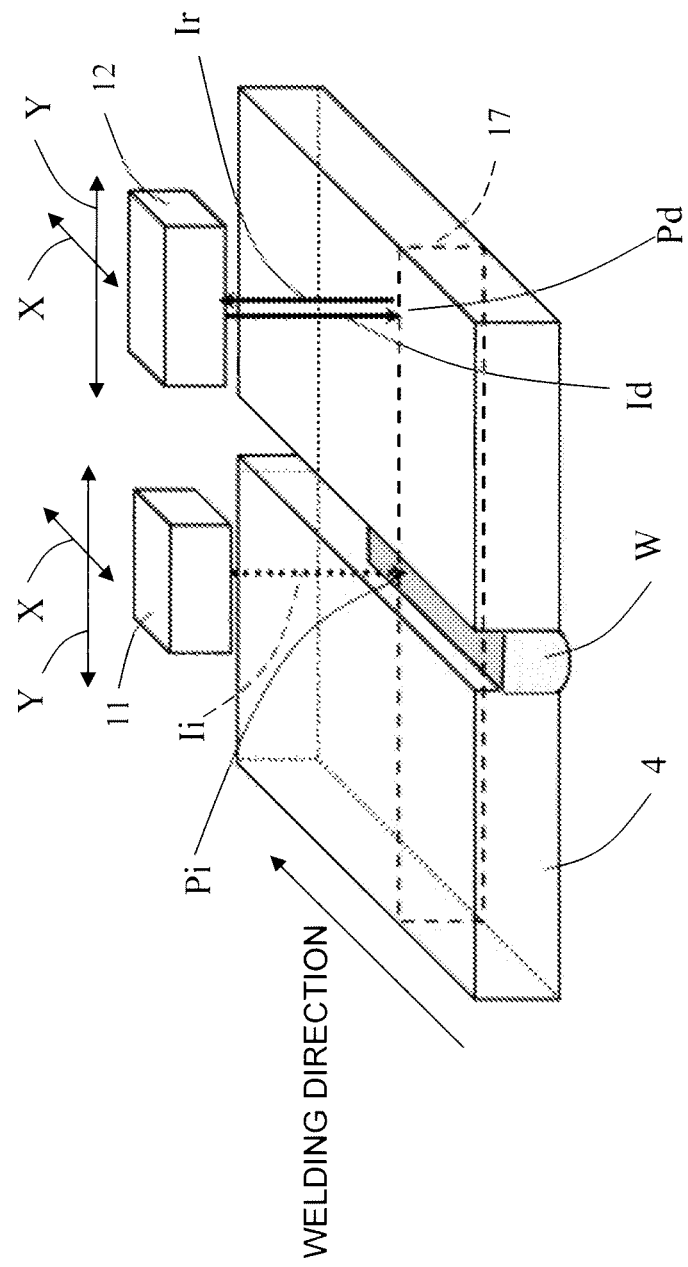
FIG. 15 is a perspective view schematically illustrating a positional relationship among the welded part, the transmission laser light irradiation point, the reception laser light irradiation point in the welding inspection apparatus according to the seventh embodiment of the present invention.
Figure 16:
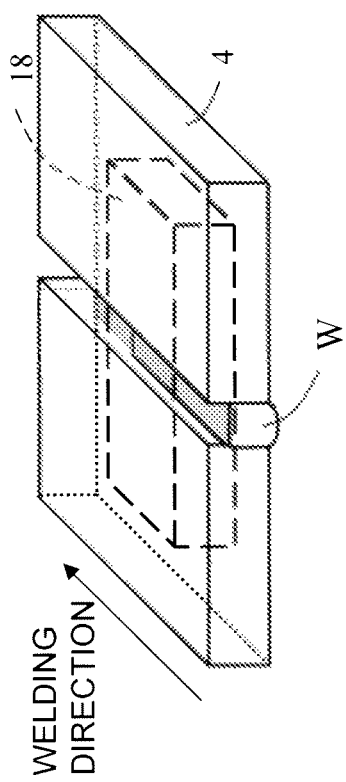
FIG. 16 is a perspective view schematically illustrating a positional relationship between two-dimensional cross-sections visualized near the welded part which is obtained by the welding inspection apparatus according to the seventh embodiment of the present invention.
Figure 17:
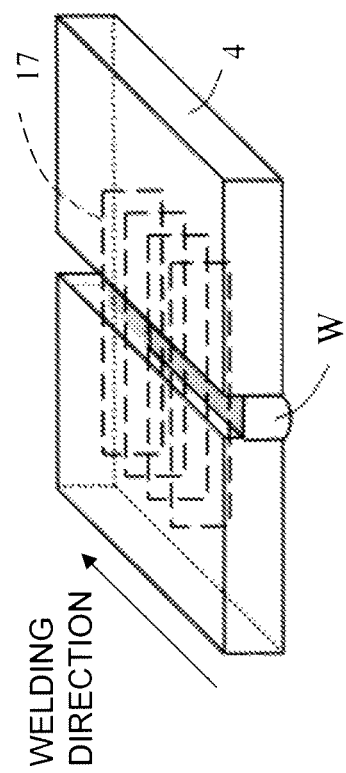
FIG. 17 is a perspective view schematically illustrating the position of a three-dimensional region visualized near the welded part which is obtained by the welding inspection apparatus according to the seventh embodiment of the present invention.
Figure 18:
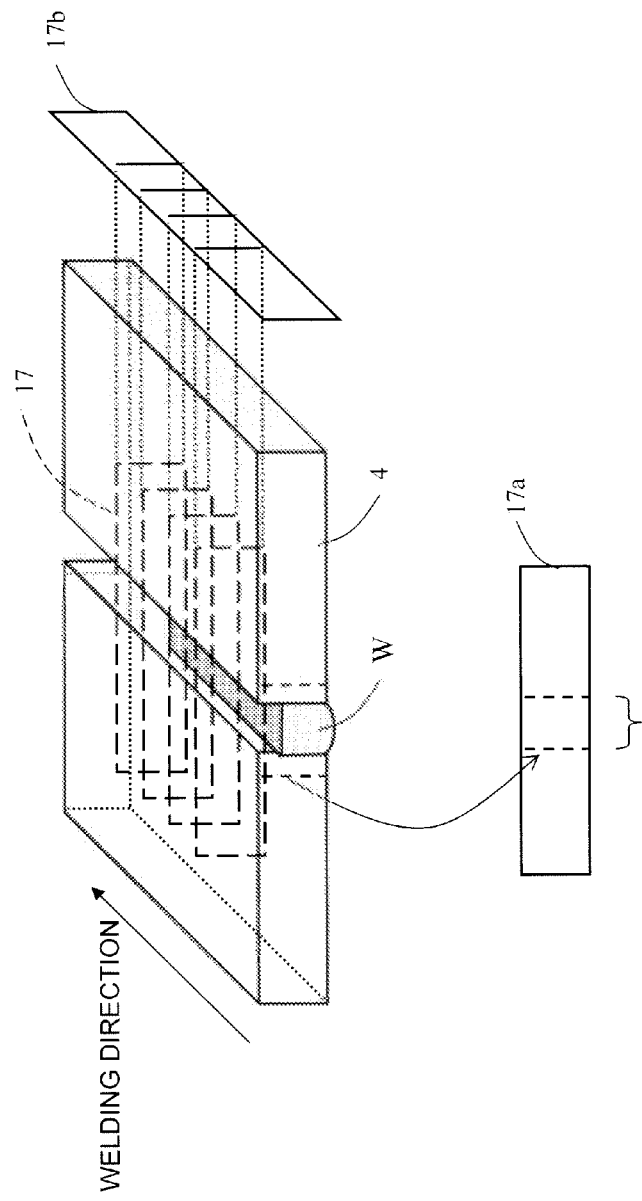
FIG. 18 is a perspective view schematically illustrating a situation where data of the visualized two-dimensional cross-sections of FIG. 16 is processed so as to be displayed (projected in a predetermined direction)

FIG. 14 is a plan view illustrating a positional relationship among the welded part W, the transmission laser light irradiation point Pi, the reception laser light irradiation point Pd in the welding inspection apparatus according to a seventh embodiment of the present invention. FIG. 15 is a perspective view schematically illustrating a positional relationship among the welded part W, the transmission laser light irradiation point Pi, the reception laser light irradiation point Pd in the welding inspection apparatus according to the seventh embodiment of the present invention. FIG. 16 is a perspective view schematically illustrating a positional relationship between two-dimensional cross-sections visualized near the welded part W which is obtained by the welding inspection apparatus according to the seventh embodiment. FIG. 17 is a perspective view schematically illustrating the position of a three-dimensional region visualized near the welded part W which is obtained by the welding inspection apparatus according to the seventh embodiment. FIG. 18 is a perspective view schematically illustrating a situation where data of the visualized two-dimensional cross-sections of FIG. 16 is processed so as to be displayed (projected in a predetermined direction).

The present embodiment is a modification of, e.g., the fifth embodiment, in which the positions of the transmission laser light irradiation point Pi and the reception laser light irradiation point Pd are changed by the transmission optical system drive mechanism 11 and the reception optical system drive mechanism 12, respectively.

In the inspection of the welded part W, data recording is performed while moving the transmission optical system drive mechanism 11 and the reception optical system drive mechanism 12 generally in the direction parallel to the welding direction, i.e., X-direction in FIGS. 14 and 15, and inspection results such as A-scan, B-scan, C-scan, and D-scan are displayed for determination of presence/absence of the defect. The A-scan, B-scan, . . . , etc., are terms used in the field of ultrasonic technology. For example, the A-scan is waveform data defined by a time axis and an ultrasonic amplitude axis, and B-scan displays waveform data with the number of elements (or positions of elements) plotted on one axis and ultrasonic amplitude (or brightness value change) plotted on the other axis. Details are described in, e.g., "Nondestructive Inspection Technique—Ultrasonic Inspection III" published by Japanese Society for Non-Destructive Inspection.

When operation of moving the transmission optical system drive mechanism 11 and the reception optical system drive mechanism 12 in the direction perpendicular to the welding direction, i.e., Y-direction in FIGS. 14 and 15 is added, inspection of a region of a two-dimensional cross-section 17 illustrated in FIGS. 15 and 16 or a portion of the region of the two-dimensional cross-section 17 that is near the welded part W can be visualized by the aperture synthesis processing.

The aperture synthesis is a technique that synthesizes data obtained by receivers at a plurality of positions so as to increase the resolving power and is used in general in an aperture synthesis radar.

A three-dimensional region 18 illustrated in FIG. 17 can also be visualized by the aperture synthesis processing.

Further, as illustrated in FIG. 18, a configuration may be possible in which a part of the visualized region of the two-dimensional cross-section 17 obtained as illustrated in FIG. 16 is subjected to signal processing such as maximum value detection processing or averaging processing and then projected in the welding direction so as to be displayed as a two-dimensional cross-section 17a. Similarly, a part of the visualized region of the two-dimensional cross-section 17 may be projected in the direction perpendicular to the welding direction so as to be displayed as a two-dimensional cross-section 17b.

The inspection can be performed during the welding operation with the results obtained by the above processing displayed on the display mechanism 8 (refer to, e.g., FIG. 1). This processing is a technique capable of significantly enhancing the detection sensitivity of the ultrasonic wave. With the above configuration, there can be provided a system capable of preventing a reduction in the sensitivity and providing a high-sensitivity inspection result.

[Eighth Embodiment]

Figure 19:
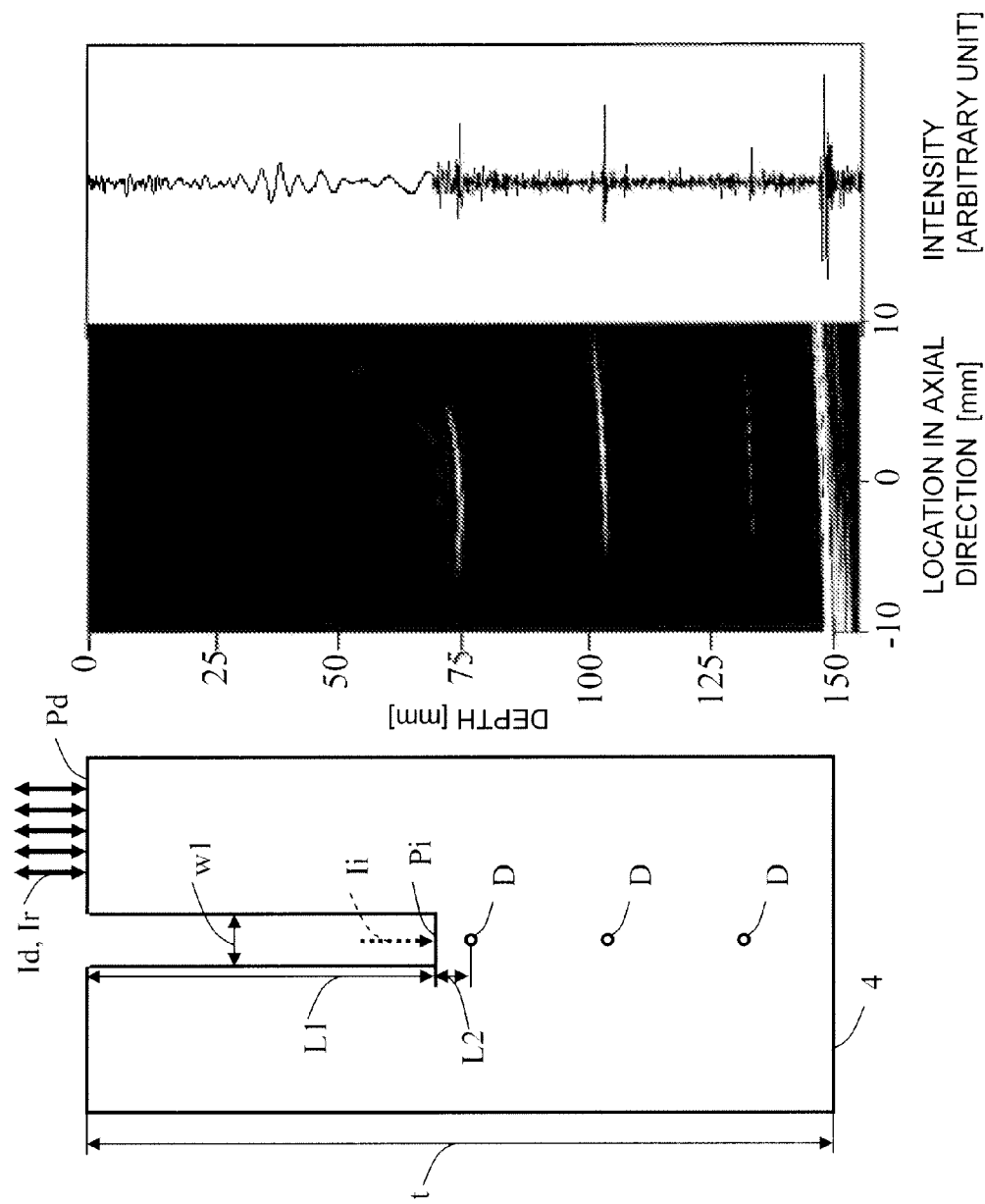
FIG. 19 is a view illustrating an example of a B-scan result in the case where aperture synthesis processing was applied by the welding inspection apparatus according to an eighth embodiment of the present invention.
Figure 20:
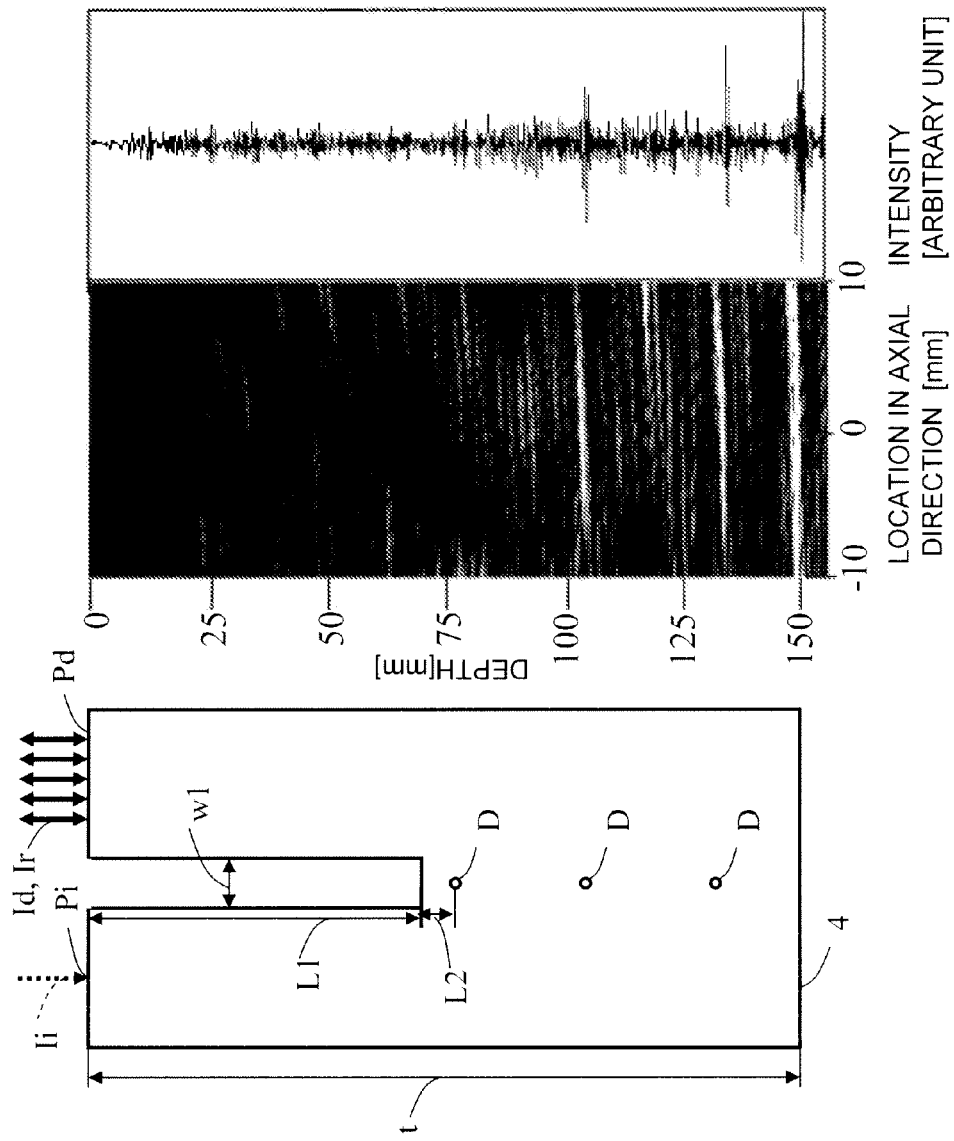
FIG. 20 is a view illustrating, as a comparison example with respect to FIG. 19, an example of a measurement result using a two-contact method in which two probes were disposed astride a welding line.

FIG. 19 is a view illustrating an example of a B-scan result in the case where the aperture synthesis processing was applied by the welding inspection apparatus according to the eighth embodiment of the present invention. FIG. 20 is a view illustrating, as a comparison example with respect to FIG. 19, an example of a measurement result using a two-contact method in which two probes were disposed astride a welding line.

The eighth embodiment uses an apparatus obtained by embodying the welding inspection apparatus of the seventh embodiment and represents a result of the measurement for a simulation test object. That is, in the eighth embodiment, the object to be inspected is obtained by adding, to a test object having a thickness t of 150 mm, a groove depth L1 of 70 mm, and a groove width w1 of 10 mm in which a state where thick welding is being performed is simulated, at a position having a depth d of 1.6 mm from the welding point, a circular-shaped defect having a diameter d of 1.6 mm diameter.

FIG. 19 illustrates a B-scan result in the case where ultrasonic waves were received at 150 points and the aperture synthesis processing was performed. FIG. 20 illustrates a result of measurement using a conventional two-probe method in which two probes were disposed astride a welding line, in which a defect just below the groove could not be detected. FIG. 19 illustrates a measurement result obtained by directly irradiating a narrow groove portion with the transmission laser light in the present embodiment, in which it could be confirmed that the defect just below the groove was detectable. This method can be applied not only to a situation where the welding operation is being performed but also to the overall structures of a type like the present test object, and it was confirmed that a defect occurring at a portion which had been blind in a conventional approach could be detected.

[Ninth Embodiment]

Figure 21:
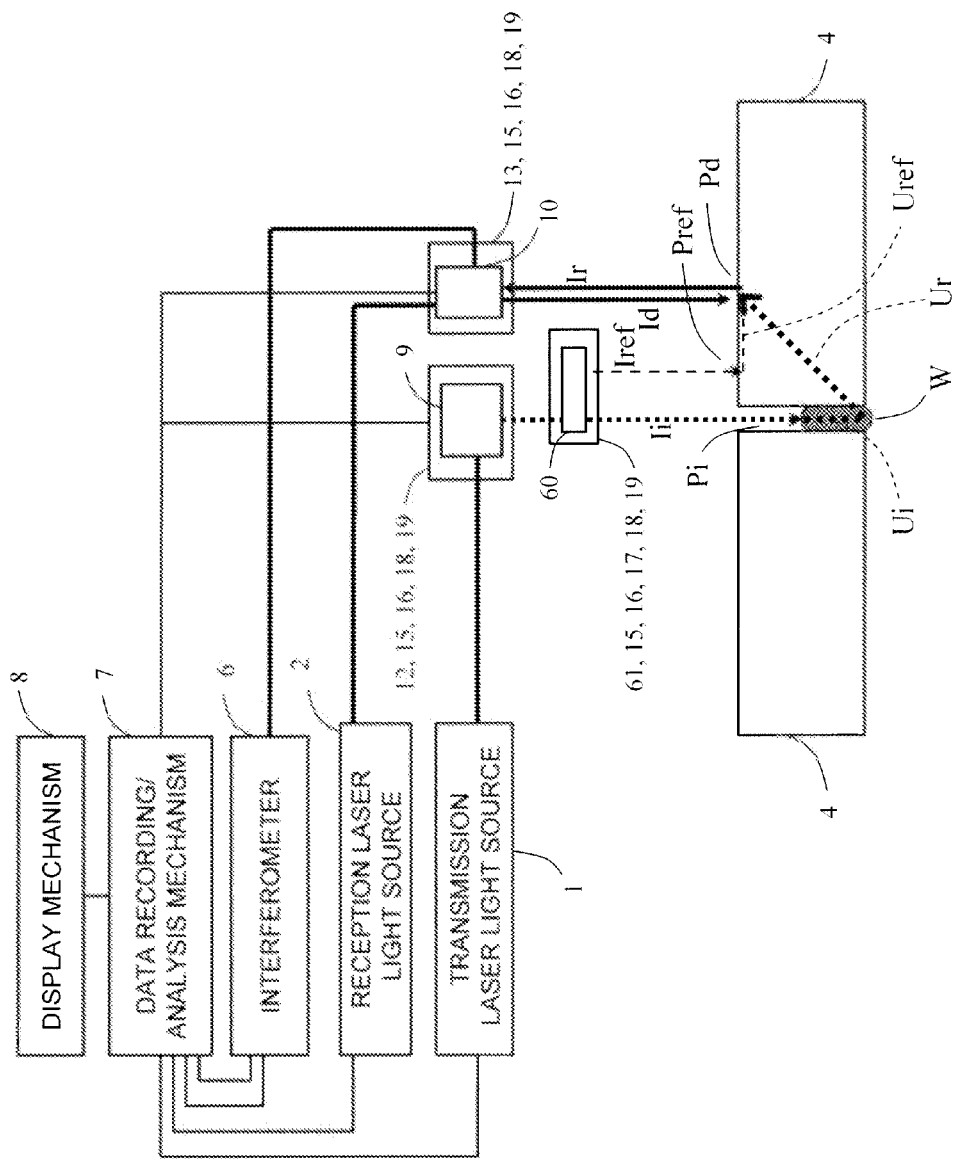
FIG. 21 is a block configuration diagram schematically illustrating a ninth embodiment of the welding inspection apparatus according to the present invention.
Figure 22:
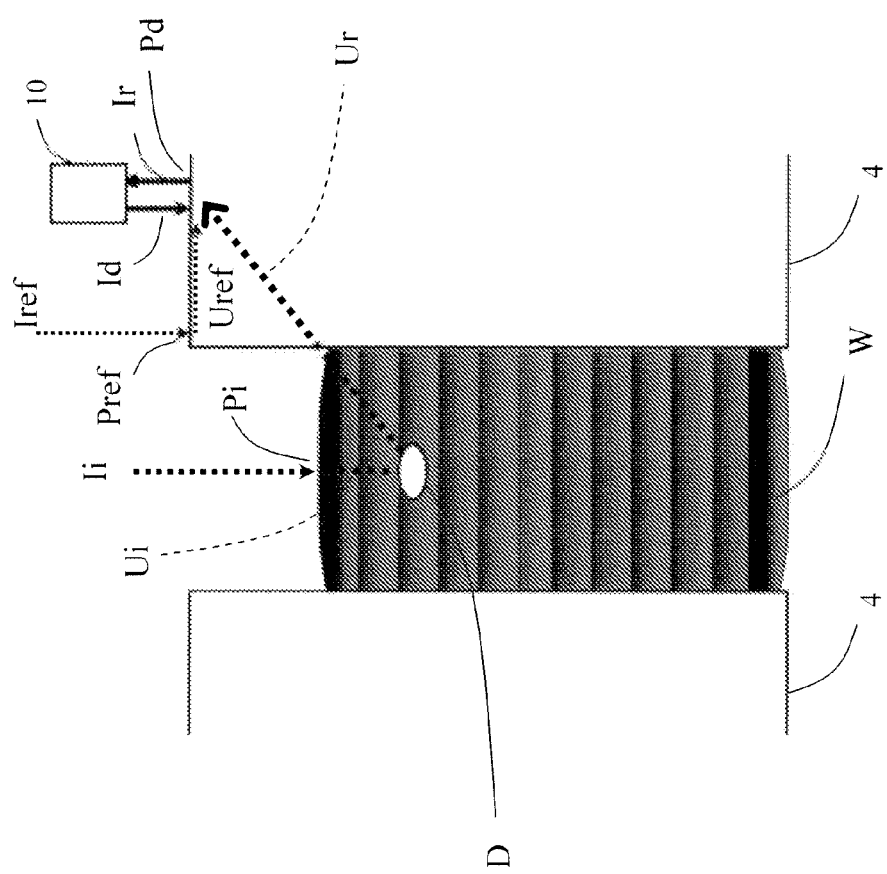
FIG. 22 is a block configuration diagram in which the main part of FIG. 21 is enlarged.

FIG. 21 is a block configuration diagram schematically illustrating a ninth embodiment of the welding inspection apparatus according to the present invention. FIG. 22 is a block configuration diagram in which the main part of FIG. 21 is enlarged.

The present embodiment is a modification of the first embodiment illustrated in FIGS. 1 and 2 and differs from the first embodiment in that an optical mechanism 60 for reference signal and an optical system drive mechanism 61 for reference signal are newly provided.

The optical mechanism 60 for reference signal generates laser light Iref for reference signal from a part of the transmission laser light Ii emitted from the transmission laser light source 1 and transmits the generated laser light Iref for reference signal to a laser irradiation point Pref for reference signal on the surface of the object 4 to be welded. The laser irradiation point Pref for reference signal is disposed at a different position from any of the transmission laser light irradiation point Pi and the reception laser light irradiation point Pd. It is preferable that the reception laser light irradiation point Pd and the laser irradiation point Pref for reference signal are disposed on the same side with respect to the welding line.

The optical system drive mechanism 61 for reference signal drives the optical mechanism 60 for reference signal and is designed to move, together with the welding mechanism 3 (refer to FIG. 10), in the welding direction relative to the object 4 to be inspected in conjunction with the transmission optical system drive mechanism 11 and the reception optical system drive mechanism 12.

The transmission laser light Ii emitted from the transmission laser light source 1 passes through the transmission optical mechanism 9 and is irradiated onto the transmission laser light irradiation point Pi on the surface of the object 4 to be inspected. At this time, ultrasonic wave Ui is generated due to reactive force against heat strain or abrasion of the superficial layer. The ultrasonic wave Ui generated includes various modes such as a longitudinal wave, a transverse wave, and a surface wave and is hereinafter collectively referred to as ultrasonic wave Ui. When the generated ultrasonic wave Ui reaches an improperly welded part or bottom surface of the object to be inspected, the propagation path changes due to reflection, scattering, and refraction of the ultrasonic wave Ui, and the ultrasonic wave Ui returns from the improperly welded part as response ultrasonic wave Ur. The response ultrasonic wave generated includes various modes such as a longitudinal wave, a transverse wave, and a surface wave and is hereinafter collectively referred to as ultrasonic wave Ur.

Further, the transmission laser light Ii emitted from the transmission laser light source 1 is separated by the optical mechanism 60 for reference signal. The optical mechanism 60 for reference signal generates laser light Iref for reference signal from a part of the transmission laser light Ii, and the generated laser light Iref for reference signal is irradiated onto the laser irradiation point Pref for reference signal on the surface of the object 4 to be inspected. At this time, a reference signal Uref is generated due to reactive force against heat strain or abrasion of a superficial layer. The reference signal Uref generated includes various modes such as a longitudinal wave, a transverse wave, and a surface wave and is hereinafter collectively referred to as reference signal Uref.

Meanwhile, the reception laser light Id emitted from the reception laser light source 2 passes through the reception optical mechanism 10 and is irradiated onto the reception laser light irradiation point Pd on the surface of the object 4 to be inspected. At this time, when the ultrasonic waves Ur and Uref reach the reception laser light irradiation point Pd, the reception laser light Id undergoes amplitude modulation or phase modulation, or a change in the reflection angle and reflected as the laser light Ir containing an ultrasonic signal component.

The laser light Ir having the ultrasonic signal is collected once again by the reception optical mechanism 10 and then transmitted to the interferometer 6. The optical signal having the ultrasonic component is converted into an electrical signal by the interferometer 6 and then stored as the ultrasonic wave data by the data recording mechanism 7.

The data recording mechanism 7 can apply averaging processing, moving average processing, filtering, FFT, wavelet transformation, aperture synthesis processing, and other signal processing to the obtained ultrasonic signal. The intensity of the obtained reference signal Uref can be measured using peak detection, integration, RMS, or other detection methods. Further, the ultrasonic signal can be corrected using the signal intensity of the reference signal Uref, welding position information, irradiation position information, temperature information, and the like. Further, a detected defect can be evaluated quantitatively by normalizing the signal intensity after correction and applying the normalized signal intensity to a DAC curve, a DGS diagram, or other calibration curves created by Calibration TP. There may be a case where the reference signal Uref is superimposed in some region to be measured; however, in this case, the reference signal Uref can be canceled as a signal appearing in a known time zone.

Advantages of the ninth embodiment will be here described. In the abovementioned first embodiment, a separate sound source serving as a reference for quantitative evaluation of the defect is not provided. In that case, a significant fluctuation occurs in a measurement system typified by a laser interferometer, so that although defect detection can be made, the quantitative evaluation thereof is difficult, resulting in failure to make accurate evaluation of the soundness of the welded part. Although it can be considered that a reflected wave from the bottom surface is used, a uniform reflected light cannot always be obtained due to a difference in the penetration shape, so that accuracy is degraded.

In the ninth embodiment, in addition to the irradiation of the transmission laser light Ii and the reception laser light Id, the laser light Iref for reference signal is irradiated onto the laser irradiation point Pref for reference signal near the transmission laser light irradiation point Pi.

The reference signal Uref propagates along the surface of the object 4 to be inspected and is received by the reception laser light Id together with the ultrasonic wave Ui. The laser ultrasonic wave is significantly influenced by a fluctuation of a measurement system, especially by fluctuation in the sensitivity of the reception side. Thus, the reception of the reference signal Uref which is excited with a constant intensity and propagates a fixed propagation path makes it possible to quantify a fluctuation on the reception side, and normalization using the intensity of the reference signal Uref allows the fluctuation to be recorrected after the measurement. With this configuration, the signal intensity can be quantitatively represented, thereby allowing quantitative evaluation of the defect to be performed based on a calibration curve such as a DAC curve or a DGS diagram.

Figure 23:
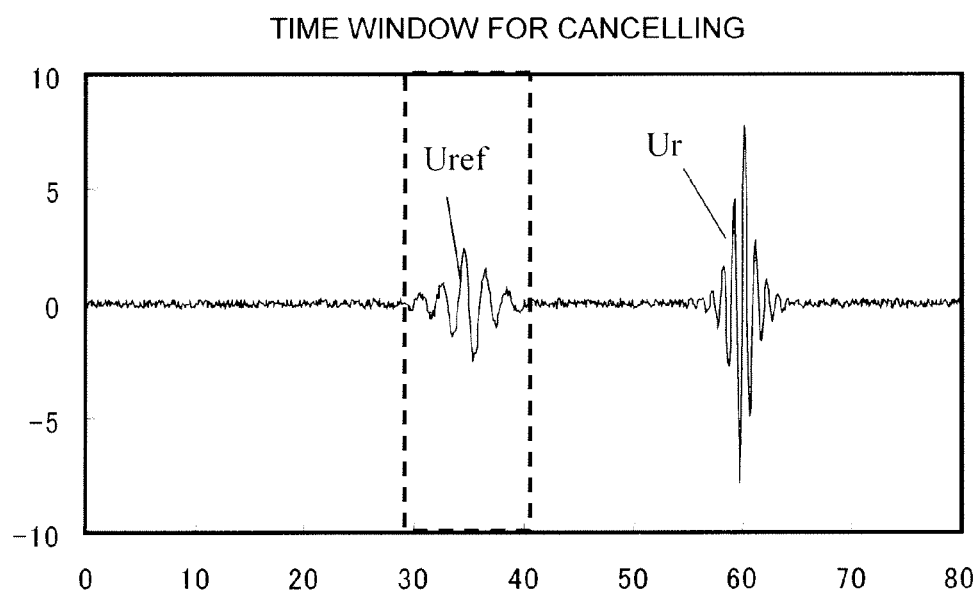
FIG. 23 is a graph illustrating an example of a measurement result obtained by the welding inspection apparatus of FIG. 21.
Figure 24:
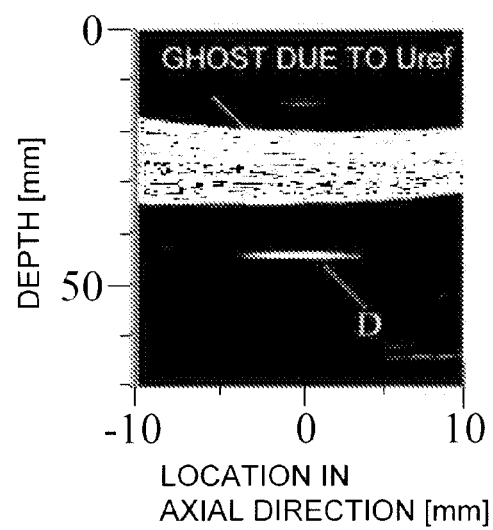
FIG. 24 is a view illustrating an example of the two-dimensional cross-section data obtained by directly processing the measurement result of FIG. 23.

FIG. 23 is a graph illustrating an example of a measurement result obtained by the welding inspection apparatus according to the ninth embodiment (FIGS. 21 and 22). FIG. 24 is a view illustrating an example of the two-dimensional cross-section data obtained by directly processing the measurement result of FIG. 23. As illustrated in FIGS. 23 and 24, in the case where the reference signal Uref is near the measurement region, the reference signal Uref may appear as ghost in the measurement result. Such ghost may cause erroneous detection.

Figure 25:
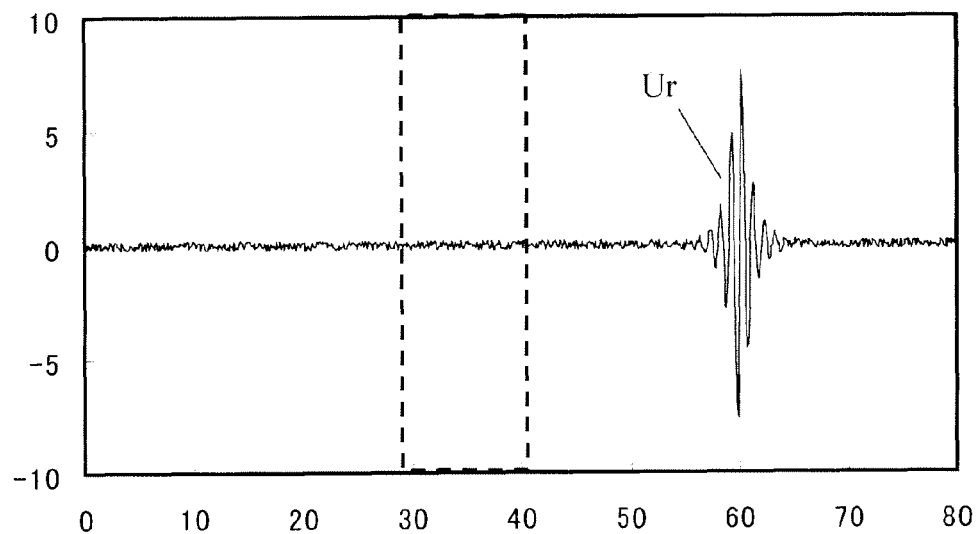
FIG. 25 is a graph illustrating an example of a result obtained by canceling the Uref from the measurement result of FIG. 23.
Figure 26:
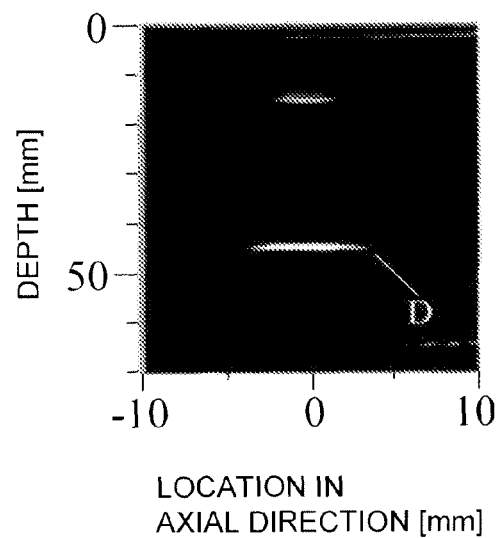
FIG. 26 is a view illustrating an example of the two-dimensional cross-section data obtained from the measurement result of FIG. 25.

To cope with the ghost of the reference signal Uref appearing in a known time zone, a time frame in which the Uref is canceled is set, whereby the influence of the ghost on the measurement result can be reduced. FIG. 25 is a graph illustrating an example of a result obtained by canceling the Uref from the measurement result of FIG. 23. FIG. 26 is a view illustrating an example of the two-dimensional cross-section data obtained from the measurement result of FIG. 25.

In the above description, the laser light Iref for reference signal is separated from the transmission laser light Ii; alternatively, as a modification, the laser light Iref for reference signal may be generated from a laser light source for reference signal separately provided from the transmission laser light source 1.

[Tenth Embodiment]

Figure 27:
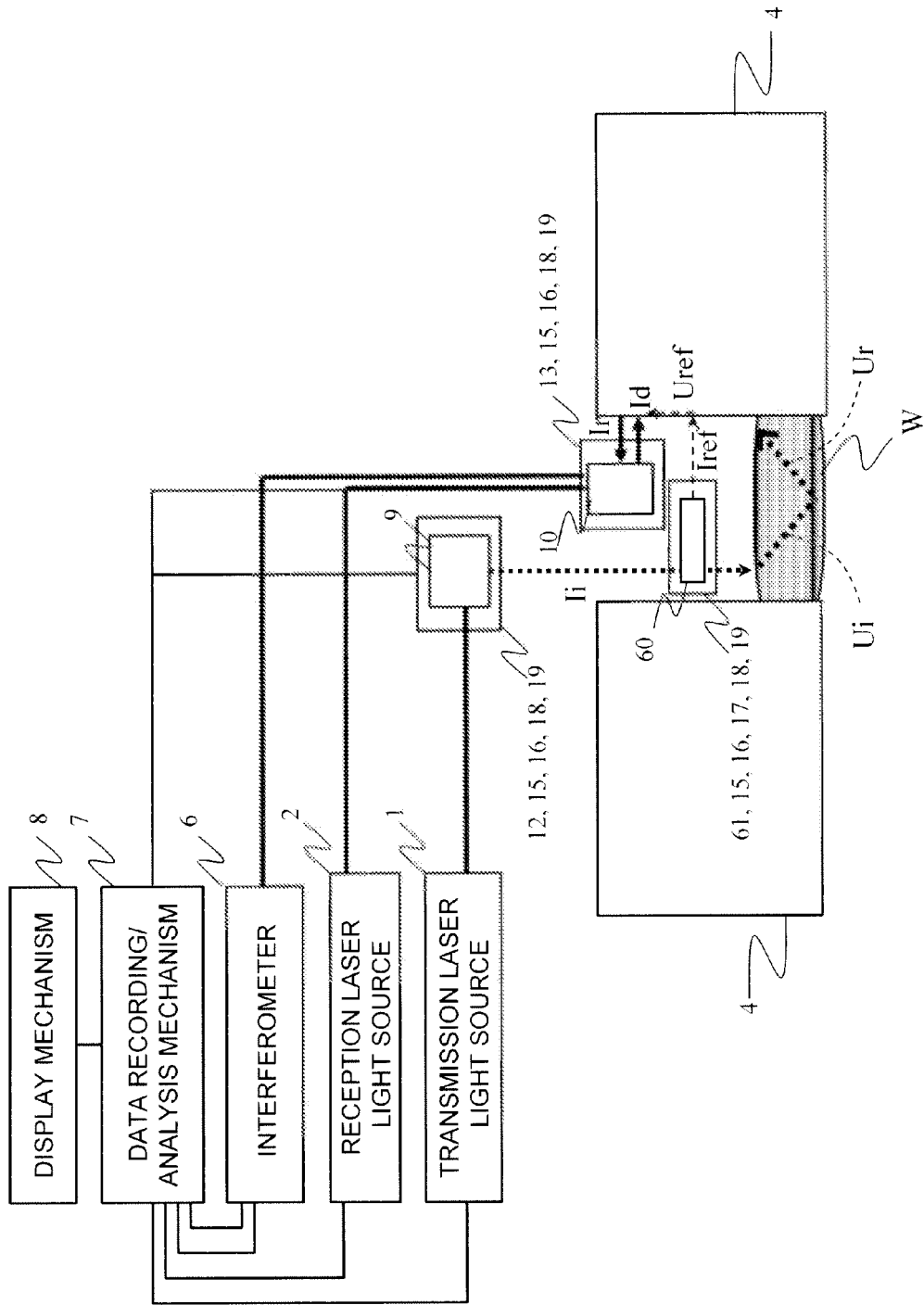
FIG. 27 is a block configuration view schematically illustrating a tenth embodiment of the welding inspection apparatus according to the present invention.
Figure 28:
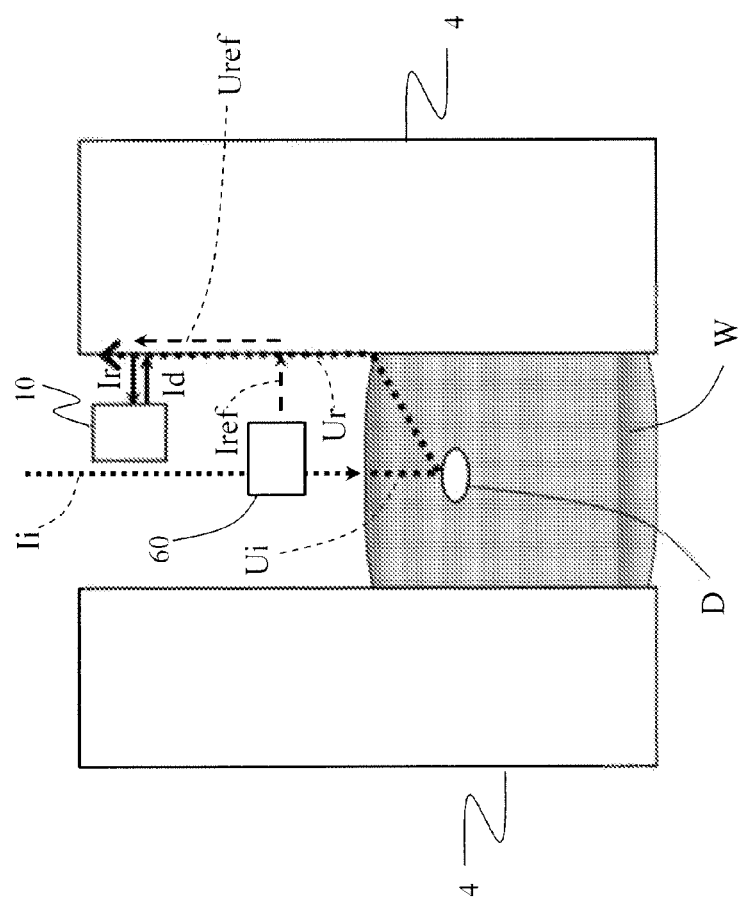
FIG. 28 is a block configuration diagram in which the main part of FIG. 27 is enlarged.

FIG. 27 is a block configuration view schematically illustrating a tenth embodiment of the welding inspection apparatus according to the present invention. FIG. 28 is a block configuration diagram in which the main part of FIG. 27 is enlarged.

The present embodiment is a modification of the second embodiment illustrated in FIGS. 6 and 7 and differs from the second embodiment in that the optical mechanism 60 for reference signal and the optical system drive mechanism 61 for reference signal of the welding inspection apparatus according to the ninth embodiment (FIGS. 21 and 22) are newly provided.

The tenth embodiment is obtained by combining the features of the second and ninth embodiments. Thus, according to the tenth embodiment, both the effects of the second and ninth embodiments can be obtained.

[Eleventh Embodiment]

Figure 29:
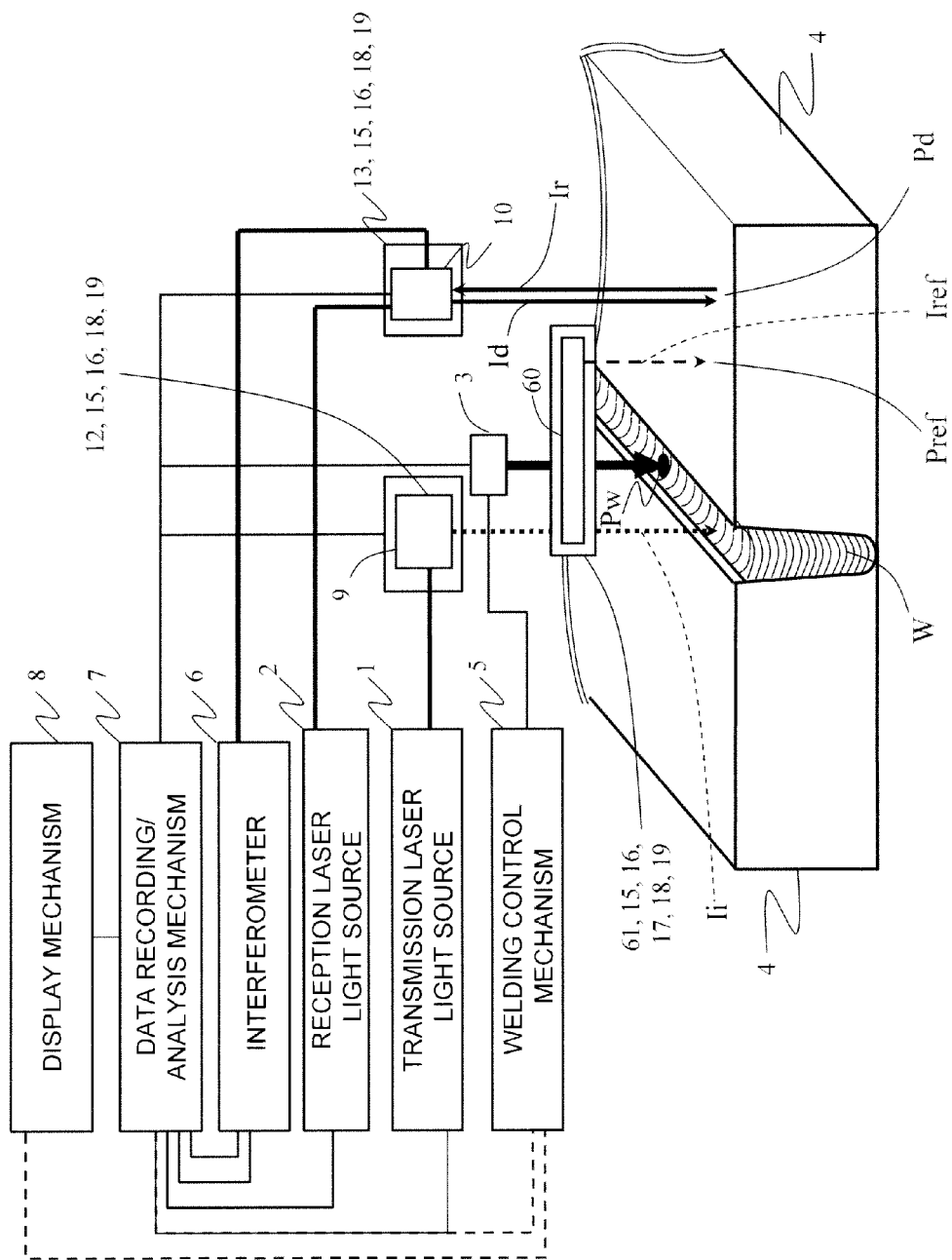
FIG. 29 is a perspective view schematically illustrating an eleventh embodiment of a welding system including the welding inspection apparatus according to the present invention.

FIG. 29 is a perspective view schematically illustrating an eleventh embodiment of a welding system including the welding inspection apparatus according to the present invention.

The present embodiment is a modification of the fifth embodiment illustrated in FIGS. 10 and 11 and differs from the fifth embodiment in that the optical mechanism 60 for reference signal and the optical system drive mechanism 61 for reference signal of the welding inspection apparatus according to the ninth embodiment (FIGS. 21 and 22) are newly provided.

The eleventh embodiment is obtained by combining the features of the fifth and ninth embodiments. Thus, according to the eleventh embodiment, both the effects of the fifth and ninth embodiments can be obtained.

[Twelfth Embodiment]

Figure 30:
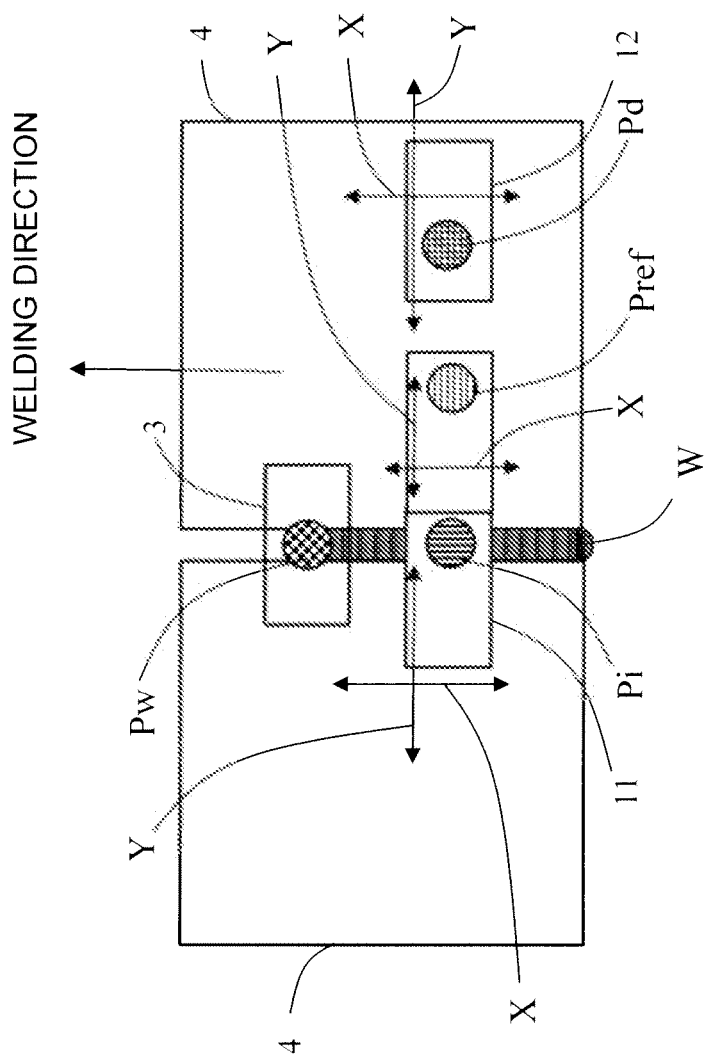
FIG. 30 is a plan view schematically illustrating a positional relationship among the welded part, the transmission laser light irradiation point, the laser light irradiation point for reference signal, and the reception laser light irradiation point in the welding inspection apparatus according to a twelfth embodiment of the present invention.
Figure 31:
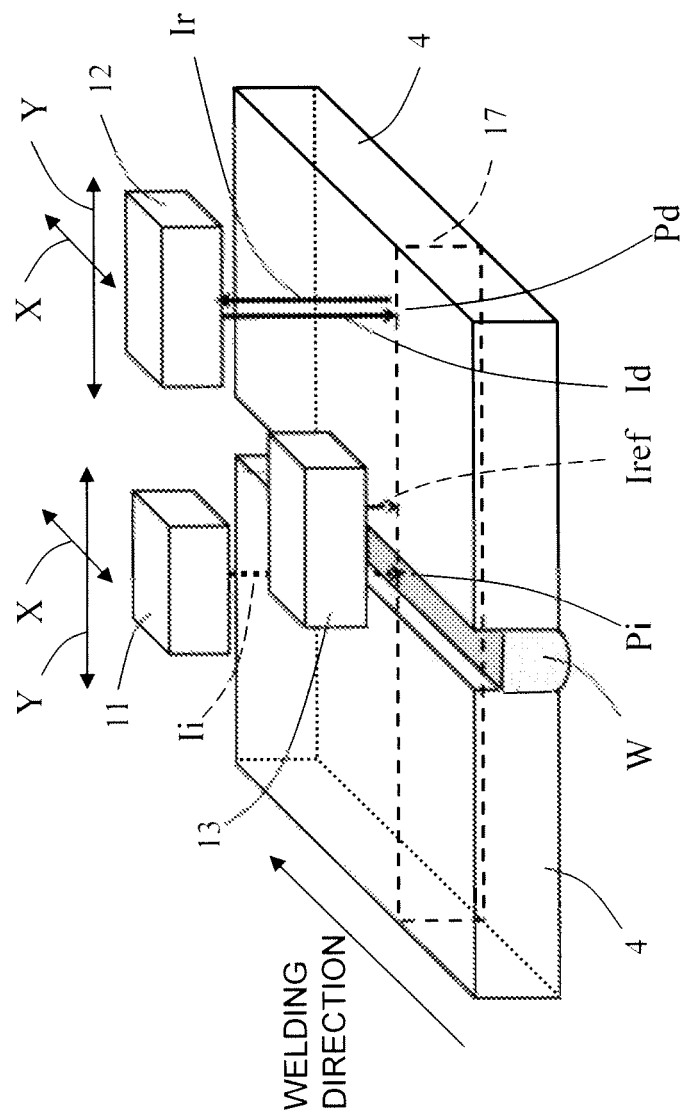
FIG. 31 is a perspective view schematically illustrating a positional relationship among the welded part, the transmission laser light irradiation point, the laser light_irradiation point for reference signal, and the reception laser light irradiation point in the welding inspection apparatus according to the twelfth embodiment of the present invention.

FIG. 30 is a plan view schematically illustrating a positional relationship among the welded part, the transmission laser light irradiation point, the laser light irradiation point for reference signal, and the reception laser light irradiation point in the welding inspection apparatus according to a twelfth embodiment of the present invention. FIG. 31 is a perspective view schematically illustrating a positional relationship among the welded part, the transmission laser light irradiation point, the laser light irradiation point for reference signal, and the reception laser light irradiation point in the welding inspection apparatus of FIG. 30.

The twelfth embodiment is obtained by combining the features of the seventh and ninth embodiments. Thus, according to the twelfth embodiment, both the effects of the seventh and ninth embodiments can be obtained.

[Other Embodiments]

Although the preferred embodiments of the present invention have been described above, the embodiments are merely illustrative and do not limit the scope of the present invention. These novel embodiments can be practiced in other various forms, and various omissions, substitutions and changes may be made without departing from the scope of the invention. The embodiments and modifications thereof are included in the scope or spirit of the present invention and in the appended claims and their equivalents.

For example, although only one of the transmission laser light irradiation point Pi and the reception laser light irradiation point Pd is located on the surface of the welded metal part W of the object 4 to be inspected in the above embodiments, both of the two irradiation points Pi and Pd may be located on the welded metal part W of the object 4 to be inspected.

Further, the features of different embodiments may be combined. For example, as described above, the ninth, tenth, eleventh, and twelfth embodiments are configured to additionally include the optical mechanism 60 for reference signal and the optical system drive mechanism 61 for reference signal based on the first, second, fifth, and seventh embodiments, respectively. In addition, the configuration in which the optical mechanism 60 for reference signal and the optical system drive mechanism 61 for reference signal is newly provided may be applied to any of the third, fourth, sixth, and eighth embodiments.

Although the term "plan view" is used in the above description for descriptive purposes, the apparatus of the present invention may be placed irrespective of a direction of gravitational force.

What is claimed is:

1. A welding inspection method comprising:
    a transmission laser light irradiation step of generating a transmission laser light and transmitting the transmission laser light via an optical transmitter to a first predetermined position on an object during or after a welding operation, the transmission laser light being configured to generate an ultrasonic wave that propagates inside of the object;
    a reception laser light irradiation step of generating a reception laser light and transmitting the reception laser light via an optical transceiver to a second predetermined position on the object, the reception laser light being configured to detect the ultrasonic wave reflected at and propagating from defects inside of the object at the second predetermined position;
    a light collection step of collecting laser light scattered and reflected at a surface of the object via the optical transceiver;
    an interference measurement step of measuring an interference of the laser light collected in the light collection step, and obtaining an ultrasonic signal; and
    an analysis step of analyzing the ultrasonic signal obtained in the interference measurement step, wherein
    the object includes two bodies configured to be combined by the welding operation at abutting faces thereof and a welded metal part provided between the abutting faces of the two bodies,
    one of the transmission laser light and the reception laser light is irradiated onto the welded metal part, and the other of the transmission laser light and the reception laser light is irradiated onto a surface of one of the two bodies.

2. The welding inspection method according to claim 1, wherein
    the transmission laser light irradiation step and the reception laser light irradiation step are performed simultaneously with the welding operation.

3. The welding inspection method according to claim 1, further comprising a temperature measurement step of measuring a temperature of a portion near propagation positions of the transmission laser light and the reception laser light, wherein
    the analysis step performs an inspection of the object to be inspected using sound velocity at the temperature obtained by the temperature measurement step.

4. The welding inspection method according to claim 1, further comprising a step of cooling the optical transmitter used in the transmission laser light irradiation step, the optical transceiver used in the reception laser light irradiation step and the light collection step, or a combination thereof.

5. The welding inspection method according to claim 1, wherein
    the transmission laser light irradiation step, the reception laser light irradiation step, and the light collection step each comprises:
    a distance measurement step of measuring a distance between the optical transmitter or the optical transceiver and the object to be inspected, and
    a focus adjustment step of performing a focus adjustment depending on the measured distance so as to make a size of a shape of the irradiation of the transmission laser light or the reception laser light incident on the object to be inspected fall within a predetermined range.

6. The welding inspection method according to claim 1, wherein
the analysis step includes a step of performing an averaging processing or an aperture synthesis processing for the ultrasonic signal.

7. The welding inspection method according to claim 1, further comprising a reference signal laser light irradiation step of irradiating with a laser light for a reference signal, during or after the welding operation, on a reference laser light irradiation position, which is a portion located on a surface of the object to be inspected and is different both from the first and second predetermined positions, wherein
the light collection step collects the laser light that has been subjected to both modulation given by a reflected ultrasonic wave obtained as a result of scattering/reflection of the ultrasonic wave generated by the irradiation of the transmission laser light, and modulation given by a reflected ultrasonic wave obtained as a result of scattering/reflection of an ultrasonic wave for the reference signal generated by the irradiation of the laser light for the reference signal.

8. The welding inspection method according to claim 7, wherein
the reference signal laser light irradiation step includes a step of generating the laser light for the reference signal by separating a part of the transmission laser light.

9. The welding inspection method according to claim 1, wherein each of the two bodies further comprises a side surface different from the abutting surface,
wherein the surface of one of the two bodies irradiated with the other of the transmission laser light and the reception laser light is the side surface.

10. A welding inspection method comprising:
a transmission laser light irradiation step of generating a transmission laser light for generating an ultrasonic wave, and transmitting the transmission laser light for irradiation via an optical transmitter to a first predetermined position on an object to be inspected during or after a welding operation;
a reception laser light irradiation step of generating a reception laser light for detecting the ultrasonic wave excited by the transmission laser light irradiation step, and transmitting the reception laser light for irradiation via an optical transceiver to a second predetermined position on the object to be inspected;
a light collection step of collecting laser light scattered and reflected at a surface of the object to be inspected via the optical transceiver;
an interference measurement step of performing an interference measurement of the laser light collected by the light collection step, and obtaining an ultrasonic signal;
an analysis step of analyzing the ultrasonic signal obtained by the interference measurement step; and
a reference signal laser light irradiation step of irradiating with a laser light for a reference signal, during or after the welding operation, on a reference laser light irradiation position, which is a portion located on a surface of the object to be inspected and is different both from the first and second predetermined positions, wherein
at least one of the transmission laser light generated in the transmission laser light irradiation step and the reception laser light generated in the reception laser light irradiation step is irradiated onto a welded metal part or a groove side surface adjacent to the welded metal part,
the light collection step collects the laser light that has been subjected to both modulation given by a reflected ultrasonic wave obtained as a result of scattering/reflection of the ultrasonic wave generated by the irradiation of the transmission laser light, and modulation given by a reflected ultrasonic wave obtained as a result of scattering/reflection of an ultrasonic wave for the reference signal generated by the irradiation of the laser light for the reference signal, and
the second predetermined position and the reference laser light irradiation position are disposed on a same side with respect to a welding line and the first predetermined position is disposed on a different side, with respect to the welding line, from the second predetermined position and the reference laser light irradiation position.

11. A welding inspection apparatus for inspecting an object, the apparatus comprising:
a transmission laser light source located at a first position and configured to generate a transmission laser light for generating an ultrasonic wave that propagates inside of the object;
an optical transmitter configured to transmit the transmission laser light to a first predetermined position on the object during or after a welding operation;
a reception laser light source located at a second position, different from the first position, and configured to generate a reception laser light, the reception light being configured to detect the ultrasonic wave reflected at and propagating from defects inside of the object;
an optical transceiver configured to transmit the reception laser light generated by the reception laser light source to a second predetermined position on the object during or after the welding operation, and to collect laser light scattered and reflected at a surface of the object;
an interferometer configured to perform an interference measurement of the scattered and reflected laser light; and
a data analyzer configured to measure and analyze an ultrasonic signal obtained by the interferometer, wherein
the object includes two bodies configured to be combined by the welding operation at abutting faces thereof and a welded metal part provided between the abutting faces of the two bodies,
the first position and the second position are selected such that one of the transmission laser light and the reception laser light is irradiated onto the welded metal part, and the other of the transmission laser light and the reception laser light is irradiated onto a surface of one of the two bodies.

12. The welding inspection apparatus according to claim 11, further comprising a reference optical transmitter configured to transmit a laser light for a reference signal to a reference laser light irradiation position, which is a portion located on the surface of the object to be inspected and is different both from the first and second predetermined positions, so as to generate an ultrasonic wave for the reference signal, wherein
laser light collected by the optical transceiver has been subjected to both a modulation given by a reflected ultrasonic wave obtained as a result of scattering/reflection of the ultrasonic wave generated by the transmission laser light source and a modulation given by a reflected ultrasonic wave obtained as a result of scattering/reflection of the ultrasonic wave for the reference signal.

13. The welding inspection apparatus according to claim 12, wherein the reference optical transmitter is configured to generate the laser light for the reference signal by separating a part of the transmission laser light.

14. The welding inspection apparatus according to claim 12, wherein
the second predetermined position and the reference laser light irradiation position are disposed on a same side with respect to a welding line.

15. A welding inspection method for inspecting an object that is combined by abutting faces of two bodies and welding the two bodies at the faces, the method comprising:
a transmission laser light irradiation step of generating a transmission laser light for generating an ultrasonic wave, and transmitting the transmission laser light for irradiation via an optical transmitter to a first predetermined position on the object to be inspected during or after a welding operation;
a reception laser light irradiation step of generating a reception laser light for detecting the ultrasonic wave excited by the transmission laser light irradiation step, and transmitting the reception laser light for irradiation via an optical transceiver to a second predetermined position on the object to be inspected;
a light collection step of collecting laser light scattered and reflected at a surface of the object to be inspected via the optical transceiver;
an interference measurement step of performing an interference measurement of the laser light collected by the light collection step, and obtaining an ultrasonic signal; and
an analysis step of analyzing the ultrasonic signal obtained by the interference measurement step, wherein
the object to be inspected includes the two bodies and a welded metal part, and
the transmission laser light generated in the transmission laser light irradiation step is irradiated onto the welded metal part, and the reception laser light generated in the reception laser light irradiation step is irradiated onto at least one of the opposed faces of the two bodies abutting each other.

16. The welding inspection apparatus according to claim 11,
wherein each of the two bodies further comprises a side surface different from the abutting surface,
wherein the surface of one of the two bodies irradiated with the other of the transmission laser light and the reception laser light is the side surface.

17. A welding inspection apparatus for inspecting an object that is combined by abutting faces of two bodies and welding the two bodies at the faces, the apparatus comprising:
a transmission laser light source configured to generate a transmission laser light for generating an ultrasonic wave;
an optical transmitter configured to transmit the transmission laser light for irradiation to a first predetermined position on the object to be inspected during or after a welding operation;
a reception laser light source configured to generate a reception laser light for detecting the ultrasonic wave excited by the transmission laser light;
an optical transceiver configured to transmit the reception laser light generated by the reception laser light source to a second predetermined position on the object to be inspected during or after the welding operation, and to collect laser light scattered and reflected at a surface of the object to be inspected;
an interferometer configured to perform an interference measurement of the scattered and reflected laser light; and
a data analyzer configured to measure and analyze an ultrasonic signal obtained by the interferometer, wherein
the object to be inspected includes the two bodies and a welded metal part, and the transmission laser light is irradiated onto the welded metal part, and the reception laser light is irradiated onto at least one of the opposed faces of the two bodies abutting each other.

18. A welding method, comprising:
a preparing step of preparing two bodies each comprising a welding surface and a side surface different from the welding surface, the two bodies abutting each other at the welding surfaces thereof;
a welding step of welding the two bodies at the welding surfaces to combine the two bodies into the object with a welded metal part provided between the welding surfaces to form an object;
a transmission laser light irradiation step of irradiating a transmission laser light at a first predetermined position on the object during or after the welding step, the transmission laser light being configured to generate an ultrasonic wave that propagates inside of the object;
a reception laser light irradiation step of irradiating a reception laser light at a second predetermined position on the object, the reception laser light being configured to detect the ultrasonic wave that propagates inside of the object;
a light collection step of collecting the reception laser light scattered and reflected at a surface of the object;
an interference measurement step of measuring an interference of the reception laser light collected in the light collection step and obtaining an ultrasonic signal; and
an analysis step of analyzing the ultrasonic signal, wherein
one of the first predetermined position and the second predetermined position is configured to be located at the welded metal part, while the other of the first predetermined position and the second predetermined position is configured to be located at one of the side surfaces of the two bodies.

* * * * *